United States Patent
Fournial et al.

(10) Patent No.: US 9,925,135 B2
(45) Date of Patent: Mar. 27, 2018

(54) **USE OF AN EXTRACT OF PLANT ORIGIN OF *GLOBULARIA* AND METHOD FOR OBTAINING SAID EXTRACT BY IN VITRO PLANT CULTURE**

(75) Inventors: Arnaud Fournial, Paris (FR); Claire-Marie Grizaud, Plaisir (FR); Philippe Mondon, Montrouge (FR); Caroline Le Moigne, Foster City, CA (US)

(73) Assignee: Sederma, S.A.S. (FR)

( * ) Notice: Subject to any disclaimer, the term of this patent is extended or adjusted under 35 U.S.C. 154(b) by 825 days.

(21) Appl. No.: 13/981,837

(22) PCT Filed: Jan. 30, 2012

(86) PCT No.: PCT/IB2012/050424
§ 371 (c)(1),
(2), (4) Date: Jul. 25, 2013

(87) PCT Pub. No.: WO2012/104774
PCT Pub. Date: Aug. 9, 2012

(65) Prior Publication Data
US 2013/0309332 A1    Nov. 21, 2013

Related U.S. Application Data

(60) Provisional application No. 61/495,020, filed on Jun. 9, 2011.

(30) Foreign Application Priority Data

Jan. 31, 2011    (FR) ..................... 11 50739

(51) Int. Cl.
| | |
|---|---|
| *A61K 8/97* | (2017.01) |
| *A61K 8/99* | (2017.01) |
| *A61K 36/185* | (2006.01) |
| *A61Q 19/08* | (2006.01) |
| *A61Q 5/00* | (2006.01) |
| *A61Q 19/00* | (2006.01) |
| *A61Q 7/00* | (2006.01) |

(52) U.S. Cl.
CPC ............... *A61K 8/97* (2013.01); *A61K 8/99* (2013.01); *A61K 36/185* (2013.01); *A61Q 5/002* (2013.01); *A61Q 19/00* (2013.01); *A61Q 19/08* (2013.01); *A61K 2800/522* (2013.01); *A61Q 7/00* (2013.01); *A61Q 19/005* (2013.01)

(58) Field of Classification Search
None
See application file for complete search history.

(56) References Cited

U.S. PATENT DOCUMENTS

| | | |
|---|---|---|
| 2003/0082117 A1 | 5/2003 | Martin et al. |
| 2008/0003308 A1 | 1/2008 | Giuliani et al. |

FOREIGN PATENT DOCUMENTS

| | | |
|---|---|---|
| EP | 0006059 A1 | 12/1979 |
| FR | 2850572 A1 | 8/2004 |
| WO | 1994/07837 A1 | 4/1994 |
| WO | 99/13855 A1 | 3/1999 |
| WO | 200043417 A1 | 7/2000 |
| WO | 2002/066668 A2 | 8/2002 |
| WO | 2003/068141 A2 | 8/2003 |
| WO | 04/024695 A1 | 3/2004 |
| WO | 2004/024695 A1 | 3/2004 |
| WO | 2004/037184 A2 | 5/2004 |
| WO | 2004/101609 A2 | 11/2004 |
| WO | 2005048968 A1 | 6/2005 |
| WO | 2005/102266 A1 | 11/2005 |
| WO | 2006075311 A1 | 7/2006 |
| WO | 2006120646 A1 | 11/2006 |
| WO | 2007029187 A2 | 3/2007 |
| WO | 2010067327 A1 | 6/2010 |

OTHER PUBLICATIONS

Sesterhenn et al. Plant Cell Reports. Mar. 2007, vol. 26, Issue 3, pp. 365-371.*
Miyase et al. J Nat Prod. vol. 62, No. 8 (1999) 1079-1084.*
Chaudhuri, et al.; Globularifolin, a New Acyl Iridoid Glucoside from Globularia cordifolia; Helvetica Chimica Acta, Jan. 23, 1980, 63:1, pp. 117-120, XP002659492.
H. Kirmizibekmez, I. Calis, P. Akbay, 0. Sticher: "Iridoid and Bisiridoid Glycosides from Globularia cordifolia", Zeitschrift für Naturforschung C., Journal of biosciences, vol. 58c, 2003, pp. 337-341, XP002659494.

(Continued)

*Primary Examiner* — Amy L Clark
(74) *Attorney, Agent, or Firm* — Lerner, David, Littenberg, Krumholz & Mentlik, LLP

(57) ABSTRACT

According to the present invention the extract of plant origin of the *Globularia* genus is used for a non-therapeutic cosmetic treatment of the skin and/or appendages. Preferably the species is *Globularia cordifolia* and the extract is obtained by in vitro plant culture. The extract can be used in particular for preventing and/or treating skin ageing by stimulating the 10 reactions of detoxification and cellular regeneration through a hormetic type response, for improving the transparency and radiance of complexion, for preventing or treating sensitive and reactive skins, for preventing or treating rednesses, for preventing protein glycation, for increasing and/or maintaining the number of dermal stem cells, for increasing and/or maintaining the dermal macromolecules, in particular collagen and elastin, for increasing the volume of the dermis, for 15 preventing and/or treating fines lines and wrinkles, for firming skin, for preventing hair loss and/or stimulating hair regrowth. The invention also proposes an original method of obtaining the extract by in vitro plant culture of undifferenciated cells of *Globularia* and an extract of plant origin that can be obtained by such method.

5 Claims, No Drawings

(56) References Cited

OTHER PUBLICATIONS

H. Kirmizibekmez, I. Calis, S. Piacente, C. Pizza: "Phenolic compounds from Globularia cordifolia", Turk J Chem, vol. 28, 2004, pp. 455-460, XP002659493.

Harborne et al.; 6-Hydroxyluteolin and Scutellarein as Phyletic Markers in Higher Plants; Phytochemistry, Feb. 1971 (Feb. 1971), 10:2, pp. 367-378, XP002659491.

International Search Report for Application No. PCT/IB2012/050424 dated Jul. 17, 2012.

* cited by examiner

SEQUENCE LISTING

<160> NUMBER OF SEQ ID NOS: 10

<210> SEQ ID NO 1
<211> LENGTH: 6

```
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 1

Val Gly Val Ala Pro Gly
1               5

<210> SEQ ID NO 2
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 2

Lys Thr Thr Lys Ser
1               5

<210> SEQ ID NO 3
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 3

Gly Gln Pro Arg
1

<210> SEQ ID NO 4
<211> LENGTH: 5
<212> TYPE: PRT
<213> ORGANISM: artificial sequence
<220> FEATURE:
<223> OTHER INFORMATION: synthetic peptide

<400> SEQUENCE: 4

Lys Thr Thr Lys Ser
1               5

<210> SEQ ID NO 5
<211> LENGTH: 4
<212> TYPE: PRT
<213> ORGANISM: artificial sequence
<220> FEATURE:
<223> OTHER INFORMATION: synthetic peptide

<400> SEQUENCE: 5

Arg Ser Arg Lys
1

<210> SEQ ID NO 6
```

```
<211> LENGTH: 4
<212> TYPE: PRT
<213> ORGANISM: artificial sequence
<220> FEATURE:
<223> OTHER INFORMATION: synthetic peptide

<400> SEQUENCE: 6

Gly Gln Pro Arg
1

<210> SEQ ID NO 7
<211> LENGTH: 4
<212> TYPE: PRT
<213> ORGANISM: artificial sequence
<220> FEATURE:
<223> OTHER INFORMATION: synthetic peptide

<400> SEQUENCE: 7

Lys Thr Phe Lys
1

<210> SEQ ID NO 8
<211> LENGTH: 6
<212> TYPE: PRT
<213> ORGANISM: artificial sequence
<220> FEATURE:
<223> OTHER INFORMATION: Synthetic peptide

<400> SEQUENCE: 8

Gly Lys Thr Thr Lys Ser
1               5

<210> SEQ ID NO 9
<211> LENGTH: 6
<212> TYPE: PRT
<213> ORGANISM: artificial sequence
<220> FEATURE:
<223> OTHER INFORMATION: synthetic peptide

<400> SEQUENCE: 9

Val Gly Val Ala Pro Gly
1               5

<210> SEQ ID NO 10
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end
<220> FEATURE:
<221> NAME/KEY: MISC_FEATURE
<222> LOCATION: (5)..(5)
<220> FEATURE:
<221> NAME/KEY: MISC_FEATURE
<222> LOCATION: (5)..(5)
<223> OTHER INFORMATION: Xaa being either a Methionine M or a Leucine L.

<400> SEQUENCE: 10

Tyr Gly Gly Phe Xaa
1               5
```

USE OF AN EXTRACT OF PLANT ORIGIN OF *GLOBULARIA* AND METHOD FOR OBTAINING SAID EXTRACT BY IN VITRO PLANT CULTURE

CROSS-REFERENCE TO RELATED APPLICATIONS

The present application is a national phase entry under 35 U.S.C. § 371 of International Application No. PCT/IB2012/050424 filed Jan. 30, 2012, published in English, which claims priority from French Application No. FR1150739 filed Jan. 31, 2011 and U.S. Application 61/495,020 filed Jun. 9, 2011, all of which are incorporated herein by reference.

TECHNICAL FIELD

The subject matter of the present invention is a new use of an extract of plant origin of *Globularia* and a preferred method of obtaining said extract by in vitro plant culture.

The present invention concerns more generally the cosmetics industry, that produce and/or use extracts of plant origin for preventing of treating disorders of skin, scalp, mucous and appendages (such as hair, eyelashes, eyebrows, nails or hairs) of animal or human mammals.

According to the invention, "extract of plant origin" means an extract that can be obtained directly from a plant or that can be obtained by culture of plant cells or tissues.

BACKGROUND ART

In cosmetics, there are many ways to improve the overall condition of the skin, hair and nails including imparting or restoring skin tone, hydration, pigmentation or depigmentation, protection against external aggressions such as UV radiations or coldness, calming irritation, redness, acne, reducing micro-oedemas (such as bags under the eyes), reducing dark circles, signs of aging such as wrinkles, fine lines, pigmentation, restoring suppleness and elasticity, treating hair loss, acting on the adipose tissues, adding volume, density, improving the texture etc.

Since a long time and in all parts of the world, the plant kingdom is an abundant and widely used source of biologically active substances in particular in the pharmaceutical and cosmetics fields.

*Globularia* genus belongs to the Plantaginaceae family, Globularioideae subfamily, and comprises several species, including those known: *Globularia alypum, Globularia bisnagarica, Globularia cordifolia, Globularia nudicaulis, Globularia vulgaris, Globularia gracilis, Globularia repens* and *Globularia valentina*.

They are small herbaceous plants, with leaves simple, alternate, with flowers in round heads, from subtropical to temperate regions. They are found mainly in Europe and North Africa.

EP0006059 discloses a process for extracting *Globularia alypum* and *Globularia vulgaris* according to which the whole plant, stems, or the leaves are treated by means of two extraction solvents differing in polarity. The extract obtained according to this process is useful in human and veterinary therapy, in particular in the treatment of brucellosis.

Specific flavones, flavonoids, iridoids and phenolic compounds have been identified in the *Globularia* genus, and in particular in the *Globularia cordifolia* species ("6-Hydroxyluteolin and Scutellarein as phyletic markers in higher plants", in the journal Phytochemistry, vol. 10, no. 2, 1971-02, p. 367-3'78; "Globularifolin, a new acyl iridoid glucoside from *Globularia cordifolia*", Helvetica Chimica Acta, vol. 63, no. 1, Jan. 23, 1980, p. 117-120; "Phenolic compounds from *Globularia cordifolia*", Turk J Chem, vol. 28, 2004, p. 455-460 and "Iridoid and bisiridoid glycosides from *Globularia cordifolia*" Journal of biosciences, vol. 58c., 2003, p. 337-341).

SUMMARY OF THE INVENTION

The aim of the present invention is to provide a new extract of plant origin for the cosmetic industry always in demand of new active ingredients.

To this aim, the present invention proposes the use of an extract of plant origin of the *Globularia* genus for a non-therapeutic cosmetic treatment of the skin and/or appendages.

The skin is subject to many external stresses: UV, electromagnetic waves, oxidants, pollutants, biological agents, etc. These stresses induce, among other deleterious effects, micro-inflammatory phenomena that are more or less chronic and the formation of toxic products in epidermal cells or at their periphery.

Among these products are the pre-inflammatory mediators and some growth factors that cause a local over-densification of epidermal nerve endings associated with a hyper-reactivity to external stimuli. This results in lowering the threshold of the skin regarding these stimuli. It becomes very sensitive, generating discomfort but also most of the time transient rednesses.

In addition, the skin gradually accumulates debris of various origins, composed of proteins, carbohydrates and altered lipids. These components (carbonylated proteins, lipoperoxides, lipofuscin, etc.) will also act as toxins that disrupt the physiology and cellular homeostasis and modify fragile metabolic balances.

Over time, they alter mitochondrial respiration, membrane integrity, enzymatic activity, and detoxification mechanisms such as the proteasome. Such changes can cause changes in behavior of certain cells such as stem cells. As a matter of fact, the latter are in a particular environment in which the change may lead to the weakening of their character and their progenitor phenotype (cell size larger, reduction of the multipliers capacity etc.), making them less able to hold their role in the renewal of keratinocytes.

Experimental data show that mild stress received in an early stage can delay degradation and therefore skin aging, helping the body to later deal with more severe stress (external events). This phenomenon is called hormesis. It is based on the activation of detoxification mechanisms and cellular defense in response to a mild stress or in response to substances which are said to have a hormetic effect (molecules called hormetins). The hormesis will contribute to a better adaptation of the cell and thus of the body with regards to subsequent stresses, allowing it to fight more effectively against the harmful effects mentioned above.

It is thus very interesting from a cosmetic point of view to mimic the effects of hormesis to improve the physiology of the skin and allow it to better fight against future stresses and thus against skin ageing.

For a better understanding of this hormetic effect, it can be spoken of an anti-ageing vaccine. However, the hormetic effect, although showing its effect on long term (anti-aging), will also improve rapidly the condition of the skin on the short term by giving it a lower sensitivity to external stresses and by providing more transparency and brightness (or radiance) to the skin.

It is this set of original and unexpected properties that has been particularly shown for the extract of *Globularia* through a series of tests (developed below).

Thus, the detailed description given below, shows that this extract has in vivo properties completely unexpected and original in targeted technical fields, comprising increasing skin transparency and cutaneous reactivity, producing a remarkable effect on the visual quality of the skin: radiance, clarity, purity and homogeneity of color, smoothness, etc. thanks in particular to a stimulation of the hormetic defenses of the skin.

Furthermore, the *Globularia* extract of the invention has shown efficacy on dermal stem cells. Dermal stem cells are involved in healing, morphogenesis and development of the hair follicle. Other properties are linked to dermal stem cells: they are precursors of the dermis, maintain and form a reservoir of cells thanks to their potential to differentiate into several cell types.

An increased and maintained number of dermal stem cells mean more fibroblasts in good shape in the dermis and thus more macromolecules and fibers (collagen, elastin, etc.). All cosmetic applications related to the replumping of dermis can be envisaged, for example the treatment of wrinkles and fines lines, or treatment of firmness. Another application is hair regrowth that can be enhanced and/or hair loss prevented since it is known that the formation of a complete hair follicle is induced by dermal cells.

Detailed in vitro example studies are given thereafter showing that the invention can apply in particular for:
- preventing and/or treating skin ageing by stimulating the detoxification reactions and cellular regeneration through a hormetic type response; and/or
- improving the radiance and/or transparency of the complexion; and/or
- for preventing and/or treating sensitive and/or reactive skins; and/or
- for preventing and/or treating rednesses; and/or
- for preventing protein glycation; and/or
- for increasing and/or maintaining the number of dermal stem cells; and/or
- for increasing and/or maintaining the dermal macromolecules, in particular collagen and elastin; and/or
- for increasing the volume of the dermis (replumping of the dermis); and/or
- for preventing and/or treating fines lines and wrinkles; and/or
- for firming skin; and/or
- for preventing hair loss and/or stimulating hair regrowth.

Other uses are possible, whitening, moisturizing, slimming, epidermis volume increasing, acne, anti-inflammatory, etc.

Particularly in cosmetics, applications can be offered for example in the ranges of moisturizers, cleansers, cleansing, anti-aging, antioxidant, protective, restorative (hands, feet, lips), contours (face, eyes, neck, lips), makeup skin care and for appendages, including eyelashes, lip products, solar products, remodeling, plumping, reshaping, lipofiling (e.g. on the hands, chest, breasts), hair products, etc.

Preferably, the present invention is directed to the *Globularia cordifolia* species which demonstrated particularly interesting results.

*Globularia cordifolia* (or heart leaf globe daisy) is a small mountain rock plant which grows at altitudes of up to 2000 m. It survives at temperatures of −30° C. and thrives in poor chalky soils. It hails from the mountains of Europe and Central Asia.

According to other features, the extract for the invention use is preferably obtained by in vitro plant culture, more particularly by plant cell culture or by tissue culture from cellular or tissular lines from different plant organs.

The invention covers also the use of an extract obtained from the whole plant or specific parts of it, more preferably obtained from leaves.

The obtaining of extracts of plant origin by in vitro culture presents numerous advantages over the agro-industrial path (plant culture in open fields and subsequent extraction in factories). The obtained extracts are free of toxic substances (herbicides, pesticides, fertilizers, heavy metals and other contaminants, such as those that may come from plant parasite). Moreover, the strict control of in vitro culture conditions reduces the risk of spontaneous variation of the strain profile and ensures a reproducible secondary metabolites profile that corresponds to the molecules of interest sought, contrary to the culture in an open field where there is the problem of variability due to weather and geography. Furthermore, this technology overcomes obstacles such as the natural biological cycle of the plant and the seasonality of production of the secondary metabolites, thus allowing a better safety and supply rapidity.

In addition, the environmental impact is minimal avoiding consumption of arable lands and soils pollution. Furthermore, biodiversity is preserved since it takes only one plant or even a seed to initiate an in vitro culture. Finally, this technology offers the ability to direct cellular metabolism toward the production of molecules of interest (elicitation of the cultures) and to achieve some controlled and relatively rapid protocols in order to maximize yields.

Among the today existing technics in the field of in vitro plant culture, the followings can be used according to the invention:

Culture of Undifferentiated Cells:

This method involves first the creation of highly proliferative cell lines in agar medium. These lines are then grown in liquid medium in order to substantially increase the biomass. At the end of the growth cycle and environmental conditions to be defined and optimized (searching for the appropriate elicitation parameters), the cell biomass will synthesize the molecules of interest. The culture is then stopped and extracted at the optimum time to obtain an extract, said to be of plant origin, containing a maximum amount of molecules of interest. Existing cell lines already available can also be used initially.

Culture of Tissue or Organ:

This type of culture can concern the root part ("root culture") or the aerial part ("shoot culture"). In this type of method, there are cultures that have been transformed by genomics bacteria *Agrobacterium rhizogenes* (root) or *Agrobacterium tumefaciens* (stems). Roots or aerial parts cultures thus transformed have a high growth rate and are genetically very stable. They are used to synthesize the molecules of interest after optimizing the elicitation parameters. These molecules are then extracted by conventional means.

In Vitro Microspropagation Through Vegetative Multiplication, in Particular Somatic Embryogenesis:

The first step for this technique is to select a parent plant with optimal characteristics (in terms of growth and production of metabolites of interest). In embryogenesis, the next step is the induction of callus from explants from the parent plant. These undifferentiated cells can give rise to numerous somatic embryos that it will be possible to multiply and extend through successive cycles of culture. From the lines of the most proliferative and productive, seedlings are regenerated in a suitable medium and extracted in at the appropriate time for optimal production of metabolites of interest. The second step is the induction of stems with leaves from explants of the parent plant on a suitable culture medium thanks to its hormonal composition. An amplification phase of leafy stem is followed by a rooting phase to induce roots. It is then possible to regenerate plantlets in large quantities, to grow them in a suitable medium and extract the molecules of interest.

The present invention preferentially provides a method of manufacturing according to the first technique of plant culture of undifferenciated cells.

More particularly, the method is of type comprising from a line of undifferentiated plant cells:
A step of pre-cultures for increasing the biomass,
A step of cultures in a bioreactor comprising a proliferation phase and then an elicitation phase, and
A recovering step of said extract.

According to other features:
The step of pre-cultures comprises the completion of pre-cultures of increasing volumes, each pre-culture of smaller size for generating cellular biomass in sufficient quantities to inoculate the pre-culture of a larger size.

The subsequent step of cultures in bioreactor is achieved in a bioreactor inoculated with the biomass produced in the pre-culture step. After an initial phase of cell proliferation in a base medium, a medium of elicitation of secondary metabolites is added to the bioreactor. Culture is stopped when the desired level of secondary metabolites has been achieved. Preferably, to achieve this level, according to the invention, an elicitation medium deficient in sucrose and macronutrients is used.

The recovery step (or harvesting step) includes an extraction stage of this biomass by any physiologically acceptable solvent, or any mixture of these solvents. The extraction can be done by different known methods that can be combined: heat, maceration, decoction, infusion, pressure, leaching, ultrasonic, microwave, by lysing the cells by any chemical or physical appropriate method. Phase separation can be achieved by filtration or centrifugation. Alternatively, it is possible to extract the biomass with a supercritical fluid or subcritical. Alternatively also, it is possible to achieve a purification using an adsorbent resin, chromatographic methods or liquid-liquid partition.

According to a preferred embodiment, the cells are lysed in order to transfer the cell contents in water. More preferably according to the present invention, the lysis is performed by lowering to an acidic pH. After several filtrations, a sterile extract is obtained. Its pH is then adjusted advantageously according to the further use of the extract, for example at pH 4 for a cosmetic application as described below.

According to the invention, the cell line may be an existing line or a line created in a preliminary stage, with said step being performed separately in time.

According to the invention, the step of creating the cell line comprises the steps 1) induction of callus (clusters of undifferentiated cells), 2) selection of the best callus line and 3) transfer to cell suspensions and optimization of the growth parameters and production of molecules of interest (e.g. elicitation).

More particularly:
1) The induction of callus can be done with all parts of the plant, including leaf, fruit, root, bud, seed, stem, branch, and meristematic tissues, in particular cambium; preferably according to the invention, the undifferentiated cell culture is achieved from the leaves of the plant.
2) The selection of the best lines, before a transfer in liquid medium, is performed according to the invention including in particular to the following criteria: high proliferative capacity, tender and friable texture, uniform color, and good dispersion in liquid medium and long-term stability of these parameters.
3) Optimization of secondary metabolites growth and production characteristics in liquid medium for the selected lines through the choice of the most appropriate media, in a first step to ensure rapid growth of the biomass and in a second time to allow maximum efficiency of secondary metabolites synthesis by cells at the end of exponential phase. This second phase corresponds to the culture elicitation and can be achieved in different ways among those available to the skilled person. These include: the addition to the cultivation of microbial fractions, stress molecules known to direct cells to their secondary metabolism, the application to the culture of a change in temperature or pH, or an osmotic stress, the use of an impoverishment of the environment, adding to the culture of adsorbent resins, which in addition to eliciting the compounds of interest can trap them. The preferred method of elicitation according to the invention is to impoverish the culture medium in macro-elements and sugar.

Therefore another object of the invention is a method for obtaining an extract of plant origin of *Globularia* in particular for implementing the use according to the invention by in vitro plant culture, comprising from a line of undifferentiated plant cells:
A pre-culture step, designed to increase biomass;
A culture step in a bioreactor comprising a proliferation phase followed by an elicitation phase; and
A recovering step of said extract;
wherein the elicitation phase in the bioreactor step is achieved with a deficient in sucrose and macronutrients medium and in that said recovery step of said extract comprises an acid pH cell lysis.

An original cell line for producing an extract of plant origin for implementing the invention is thus obtained, original and active in the searched fields as shown by the efficacy tests given below, preferably a cell line of *Globularia cordifolia*.

Another object of the invention is thus the extract that can be obtained with the method of the invention as mentioned above.

A further object of the invention is a topical composition comprising a *Globularia* extract, and preferably a *Globularia cordifolia* extract, more preferably a *Globularia cordifolia* extract obtained by in vitro culture of undifferentiated plant cells as disclosed here-above according to the invention. Such a topical composition may comprise a physiologically acceptable medium and additional actives (as mentioned thereafter in the galenic examples). The topical composition may be used for cosmetic applications or dermo-pharmaceutical applications.

The present invention also covers an extract of plant origin obtained conventionally by solvent extraction of the whole plant or specific parts of the plant, by supercritical fluid, micro-wave or ultrasounds, but comparative results showed superiority of the extract obtained from a cell line compared to a conventional solvent extract. These results are given below in the detailed description.

The *Globularia* extract for implementing the invention can be used pure or diluted in a physiologically acceptable medium forming an excipient or matrix.

According to other advantageous features of the present invention, the extract of *Globularia* can be combined with at least one additional active ingredient, in order to preferably provide an end product with a wider range of properties. Additional active ingredients can be for example selected from whitening agents, anti-redness, UV sunscreens, moisturizing, humectant, exfoliating anti-aging, anti-wrinkles, thinning, volumizing, improving the elastic properties, anti-acne, anti-inflammatory, anti-oxidant, anti-radical, depigmenting, propigmenting, depilatories, anti-growth or promoting hair growth, peptides, vitamins agents etc. These active ingredients can be obtained from plant materials such as plant extracts or products of plant culture or fermentation.

More specifically, in a cosmetic composition, the extract of plant origin according to the invention can be combined with at least one of the compounds selected from the compounds of the B3vitamin compounds such as niacinamide and tocopherol, retinoid compounds such as retinol, hexamidine, α-lipoic acid, resveratrol or DHEA, peptides, including N-acetyl-Tyr-Arg-O-hexadecyl, Pal-VGVAPG (SEQ ID NO: 1), Pal-KTTKS (SEQ ID NO: 2), Pal-GHK, Pal-KMO2K and Pal-GQPR (SEQ ID NO: 3), which are conventional active ingredients used in topical cosmetic or dermo-pharmaceutical compositions.

The present invention will be better understood in light of the following description.

The following examples illustrate the invention without limiting it only to those applications.

DETAILED DESCRIPTION

Composition Preparation

The expression "physiologically acceptable medium" means according to the present invention, without limitation, an aqueous or hydro-alcoholic solution, a water-in-oil emulsion, an oil-in-water emulsion, a micro-emulsion, an aqueous gel, an anhydrous gel, a serum, a dispersion of vesicles or a powder.

"Physiologically acceptable" means that the compositions are suitable for topical use in contact with mucous membranes, nails, scalp, hairs, hair and skin of mammals, particularly human, without risk of toxicity, incompatibility, instability, allergic response, and others.

"The physiologically acceptable medium" forms what is commonly called the excipient of the composition.

The effective amount of the extract of plant origin for implementing the present invention, that is to say its dosage, depends on various factors such as age, the state of the patient, the severity of the disorder or condition and the mode of administration. An effective amount means a not toxic amount enough to achieve the desired effect.

In a cosmetic composition for implementing the present invention, the extract of *Globularia* to be present in an effective amount, is generally in an amount ranging from 0.000001% to 15% on the total weight of the composition, more preferably between 0.0001% and 10%, depending on the destination of the composition and the desired effect more or less pronounced.

All percentages and ratios used herein are by weight of the total composition and all measurements are made at 25° C. unless it is otherwise specified.

The choice of excipient in the composition is made according to the constraints of the active extract of *Globularia* (stability, solubility, etc.), and if necessary according to the dosage form intended further for the composition.

The *Globularia* extract of the invention may be incorporated into the composition by means of an aqueous solution, or be dissolved by the usual physiologically acceptable solubilizers, for example and without limiting to this list: ethanol, propanol, isopropanol, propylene glycol, glycerin, butylene glycol, or polyethylene glycol or any combination thereof. It may also be interesting to solubilize the extract with emulsifiers. A powder medium can also be used.

The compositions for the present invention are generally prepared by conventional methods well known to one skilled in the art for making topical and oral compositions and injection compositions. Such methods may involve a mixture of ingredients in one or more steps to obtain a uniform state, with or without heating, cooling, etc.

The different galenic forms that may contain the *Globularia* extract of the invention are all forms i.e. creams, lotions, milks or creams ointments, gels, emulsions, dispersions, solutions, suspensions, cleansers, foundations, anhydrous preparations (sticks in particular lip balm, body and bath oils), shower and bath gels, shampoo and hair care lotions, milks or creams for skin care or hair, cleansing lotions or milks, sunscreen lotions, milks or creams, artificial tanning lotions, milks or creams, pre shave, shaving or aftershave creams, foams, gels or lotions, makeup, lipstick, mascara or nail polish, skin essences, serums, adhesive or absorbent materials, transdermal patches, or emollient powders, lotions, milks or creams, sprays, body and bath oils, foundation basis, ointment, emulsion, colloid, compact suspension or solid, pencil, sprayable formulation, brushable, blush, red, eyeliner, lipliner, lip gloss, face or body powder, styling gels or mousses, nail conditioning, lip balms, skin conditioners, moisturizers, lacquers, soaps, exfoliants, astringents, depilatories agents, permanent waving solutions, antidandruff formulations, antiperspirant or antiperspirant compositions, including sticks, "roll-on" deodorants, air fresheners, sprays for the nose and etc.

These compositions may also be in the form of lipsticks intended either to color the lips or to prevent them from chapping, or makeup for eyes, eyes-shadows and foundations for the face. The compositions for the invention can include cosmetics, personal care products and pharmaceutical preparations. A composition in the form of foam or in the form of aerosol compositions also comprising a pressurized propellant can be considered.

The extract according to the present invention may be in the form of solution, dispersion, emulsion, paste, or powder, individually or as a premix or vehicled individually or as a premix in vectors such as macro-, micro-, or nanocapsules, macro-, micro- or, nanospheres, liposomes, oleosomes or chylomicrons, macro-, micro-, or nanoparticles or macro-, micro or nanosponges, spores or exines, micro or nano emulsions or adsorbed on organic polymer powders, talcs, bentonites, or other inorganic or organic supports.

The *Globularia* extract according to the present invention may be used in any form whatsoever, in a form bound to or incorporated in or absorbed in or adsorbed on macro-, micro-, and nanoparticles, or macro-, micro-, and nanocapsules, for the treatment of textiles, natural or synthetic fibers, wools, and any materials that may be used for clothing or underwear for day or night intended to come into contact with the skin, handkerchiefs or cloths, to exert their cosmetic effect via this skin/textile contact and to permit continuous topical delivery.

Additional Ingredients

The CTFA International cosmetic ingredient dictionary & handbook (13th Ed. 2010) (published by the Cosmetic, Toiletry, and Fragrance Association, Inc., Washington, D.C.) describes a non-limited wide variety of cosmetic and pharmaceutical ingredients conventionally used in the skin care industry that can be used as additional ingredients/compounds in the compositions for the present invention. Examples of these ingredient classes include, but are not limited to: healing agents, skin anti-aging agents, anti-wrinkle agents, anti-atrophy agents, skin moisturizing agents, skin smoothing agents, antibacterial agents, antiparasitic agents, antifungal agents, fungicidal agents, fungistatic agents, bactericidal agents, bacteriostatic agents, antimicrobial agents, anti-inflammatory agents, anti-pruriginous agents, anesthetic agents, antiviral agents, keratolytic agents, free radicals scavengers, anti-seborrhea agents, anti-dandruff agents, the agents modulating differentiation, proliferation or pigmentation of the skin and agents accelerating penetration, desquamating agents, melanin synthesis stimulating or inhibiting agents, whitening, depigmenting or lightening agents, pro-pigmenting agents, self-tanning agents, NO-synthase inhibiting agents, antioxidants, free radical scavengers and/or agents against atmospheric pollution, reactive carbonyl species scavengers, anti-glycation agents, tightening agents, agents stimulating the synthesis of dermal or epidermal macromolecules and/or capable of inhibiting or preventing their degradation, such as for example collagen synthesis stimulating agents, elastin synthesis stimulating agents, decorin synthesis stimulating agents, laminin synthesis stimulating agents, defensin synthesis stimulating agents, chaperone synthesis stimulating agents, aquaporin synthesis stimulation agents, hyaluronic acid synthesis stimulating agents, fibronectin synthesis stimulating agents, sirtuin synthesis-stimulating agents, agents stimulating the synthesis of lipids and components of the stratum corneum (ceramides, fatty acids, etc.), collagen degradation inhibiting agents elastin degradation inhibiting agents, agents stimulating fibroblast proliferation, agents stimulating keratinocyte proliferation, adipocyte proliferation stimulating agents, melanocyte proliferation stimulating agents, keratinocyte differentiation stimulating agents, adipocyte differentiation stimulating agents, acetylcholinesterase inhibiting agents, glycosaminoglycan synthesis stimulating agents, DNA repair agents, DNA protecting agents, anti-itching agents, agents for the treatment and/or care of sensitive skin, firming agents, anti-stretch mark agents, astringent agents, sebum production regulating agents, dermo-relaxing agents, healing adjuvant agents, re-epithelialization stimulating agents, re-epithelialization co-adjuvant agents, cytokine growth factors, calming agents, anti-inflammatory agents, agents acting on capillary circulation and/or microcirculation, angiogenesis stimulating agents, vascular permeability inhibiting agents, agents acting on cell metabolism, agents able to improve dermal-epidermal junction, agents inducing hair growth, hair growth inhibiting or retardant agents, muscle relaxants agents, antipollution and/or anti-free radical agents, lipolysis stimulating agents, slimming agents, anti-cellulite agents, agents acting on the microcirculation, agents acting on the energy metabolism of the cells, cleaning agents, hair conditioning agents, hair styling agents, hair growth promoters, sunscreen agents, total sunscreen agents, make-up agents, detergents, pharmaceutical products, emulsifiers, emollients, organic solvents, antiseptic agents, deodorant actives, physiologically acceptable carriers, surfactants, abrasives, absorbents, aesthetic components such as fragrances, pigments, dyes, colorants, natural colorants, essential oils, touch agents, cosmetic astringents, anti-acne agents, anti-coagulation agents, anti-foaming agents, antioxidants, binders, biological additives, enzymes, enzymatic inhibitors, enzyme-inducing agents, coenzymes, chelating agents, plant extracts, plant derivatives, essential oils, marine extracts, agents obtained from a bio-fermentation or a biotechnological process, mineral salts, cell extracts, sunscreens (organic or mineral photoprotective agents active against ultraviolet A and/or B rays), ceramides, peptides, buffers, volumizing agents, chelating agents, chemical additives, colorants, cosmetic biocides, denaturants, medical astringents, external analgesics, film formers, such as polymers, for exacerbing film-forming properties and substantivity of the composition, quaternary derivatives, substantivity increasing agents, opacifying agents, pH adjusters and regulators (e.g. triethanolamine), propellants, reducing agents, sequestrants, decoloring and/or lightening agents, skin-conditioning agents (e.g., humectants, including miscellaneous and occlusive), moisture retaining agents, alpha-hydroxyacids, betahydroxyacids, moisturizers, epidermal hydrolytic enzymes, healing and/or calming agents, skin treating agents, anti-wrinkle agents, agents that reduce or treat bags under the eyes, exfoliating agents, thickeners, softening agents, gellifying polymers, vitamins and their derivatives, wetting agents, peeling agents, soothing agents, curative agents of the skin, lignans, preservatives (i.e. phenoxyethanol and parabens), anti UV, cytotoxic agents, antineoplastics, viscosity modifiers, non-volatile solvents, pearling agents, anti-perspirant agents, depilatories, vaccine, perfumed water, skin restructuring agent (i.e. *Siegesbeckia orientalis* extract), excipients, charges, minerals, anti-mycobacterial agents, anti-allergenic agents, H1 or H2 antihistaminics, anti-irritants, agents stimulating the immune system, agents inhibiting the immune system, insect repellents, lubricants, pigments or dyes, hypopigmentation agents, preservatives, light stabilizers, and mixtures thereof, as long as they are physically and chemically compatible with the other ingredients of the composition and especially with the actives of the present invention.

Also the nature of these additional ingredients should not unacceptably alter the benefits of the active ingredients of the invention. These additional ingredients can be synthetic or natural such as plants extracts, or come from a bio-fermentation process. Additional examples can be found in the CTFA Cosmetic Ingredient Handbook.

Such additional active ingredient/compound can be selected from the group consisting of: sugar amines, glucosamine, D-glucosamine, N-acetyl glucosamine, N-acetyl-D-glucosamine, mannosamine, N-acetyl mannosamine, galactosamine, N-acetyl galactosamine, B3 vitamin and its derivatives, niacinamide, sodium dehydroacetate, dehydroacetic acid and its salts, phytosterols, salicylic acid compounds, hexamidines, dialkanoyl hydroxyproline compounds, soy extracts and derivatives, equol, isoflavones, flavonoids, phytantriol, farnesol, geraniol, bisabolol, peptides and their derivatives, di-, tri-, tetra-, penta-, and hexa-peptides and their derivatives, KTTKS (SEQ ID NO: 4), PalKTTKS (SEQ ID NO: 2), carnosine, N-acyl amino acid compounds, retinoids, retinyl propionate, retinol, retinyl palmitate, retinyl acetate, retinal, retinoic acid, water-soluble vitamins, ascorbates, C vitamin, ascorbyl glucoside, ascorbyl palmitate, magnesium ascorbyl phosphate, sodium ascorbyl phosphate, vitamin B and their derivatives, B1 vitamin, B2 vitamin, B6 vitamin, B12 vitamin, K vitamin and derivatives, pantothenic acid and its derivatives, pantothenyl ethyl ether, panthenol and derivatives, dexpanthenol, biotin, amino acids and their salts and derivatives, water soluble amino acids, asparagine, alanine, indole, glutamic acid, water insoluble vitamins, A vitamin, E vitamin, vitamin F, D vitamin and mono-, di-, and tri-terpenoids compounds, beta-ionol, cedrol, and their derivatives, water insoluble amino acids, tyrosine, tryptamine, particulate materials, butylated hydroxytoluene, butylated hydroxyanisole, allantoin, tocopherol nicotinate, tocopherol, tocopherol esters, pal-GHK, phytosterol, hydroxy acids, glycolic acid, lactic acid, lactobionic acid, keto acids, pyruvic acid, phytic acid, lysophosphatidic acid, stilbenes, cinnamates, resveratrol, kinetin, zeatin, dimethylaminoethanol, natural peptides, soy peptides, salts of sugar acids, Mn gluconate, Zn gluconate, piroctone olamine, 3,4,4'-trichlorocarbanilide, triclocarban, Zn pyrithione, hydroquinone, kojic acid, ascorbic acid, magnesium ascorbyl phosphate, ascorbyl glucoside, pyridoxine, aloe vera, terpene alcohols, allantoin, bisabolol, dipotassium glycyrrhizinate, glycerol acid, sorbitol acid, pentaerythritol acid, pyrrolidone acid and salts, dihydroxyacetone, erythrulose, glyceraldehyde, tartaraldehyde, clove oil, menthol, camphor, eucalyptus oil, eugenol, menthyl lactate, witch hazel distillate, eicosene and vinyl pyrrolidone copolymer, iodopropyl butylcarbamate, a polysaccharide, an essential fatty acid, a salicylate, glycyrrhetinic acid, carotenoids, ceramides and pseudo-ceramides, a lipid complex, oils in general of natural origin such shea butter, apricot oil, onagre oil, prune oil, palm oil, monoi oil, hydroquinone, HEPES, procysteine, O-octanoyl-6-D-maltose, the disodium salt of methylglycinediacetic acid, steroids such as diosgenin and derivatives of DHEA, DHEA or dehydroepiandrosterone and/or a precursor or chemical or biological derivative thereof, N-ethyloxycarbonyl-4-para-aminophenol, blueberries extracts, phytohormones, extracts of the yeast *Saccharomyces cerevisiae*, extracts of algae, extracts of soyabean, lupin, maize and/or peas, alverine and its salts, in particular alverine citrate, extract of butcher's broom and of horse chestnut, and mixtures thereof, a metalloproteinase inhibitor.

Further skin care and hair care active ingredients that are particularly useful can be found in SEDERMA commercial literature and on the website www.sederma.fr.

The following commercial actives can also be mentioned, as examples: betain, glycerol, Actimoist Bio 2™ (Active organics), AquaCacteen™ (Mibelle AG Cosmetics), Aquaphyline™ (Silab), AquaregulK™ (Solabia), Carciline™ (Greentech), Codiavelane™ (Biotech Marine), Dermaflux™ (Arch Chemicals, Inc), Hydra'Flow™ (Sochibo), Hydromoist L™ (Symrise), RenovHyal™ (Soliance), Seamoss™ (Biotech Marine), Essenskin™ (Sederma), Moist 24™ (Sederma), Argireline™ (trade name of the acetyl hexapeptide-3 of Lipotec), spilanthol or an extract of *Acmella oleracea* known under the name Gatuline Expression™, an extract of *Boswellia serrata* known under the name Boswellin™, Deepaline PVB™ (Seppic), Syn-AKE™ (Pentapharm), Ameliox™ Bioxilift™ (Silab), Juvinity™ (Sederma), Revidrat™ (Sederma), or mixtures thereof.

Among other plant extracts which can be combined with the extract of the invention, there may more particularly be mentioned extracts of Ivy, in particular English Ivy (*Hedera Helix*), of *Bupleurum chinensis*, of *Bupleurum Falcatum*, of arnica (*Arnica Montana* L), of rosemary (*Rosmarinus officinalis* N), of marigold (*Calendula officinalis*), of sage (*Salvia officinalis* L), of ginseng (*Panax ginseng*), of ginko biloba, of St.-John's-Wort (*Hyperycum Perforatum*), of butcher's-broom (*Ruscus aculeatus* L), of European meadowsweet (*Filipendula ulmaria* L), of big-flowered Jarva tea (*Orthosiphon Stamincus* Benth), of algae (*Fucus Vesiculosus*), of birch (*Betula alba*), of green tea, of cola nuts (*Cola Nipida*), of horse-chestnut, of bamboo, of *Centella asiatica*, of heather, of fucus, of willow, of mouse-ear, of escine, of cangzhu, of *chrysanthellum indicum*, of the plants of the Armeniacea genus, *Atractylodis Platicodon*, *Sinnomenum*, *Pharbitidis*, *Flemingia*, of *Coleus* such as *C. Forskohlii, C. blumei, C. esquirolii, C. scutellaroides, C. xanthantus* and *C. Barbatus*, such as the extract of root of *Coleus barbatus*, extracts of Ballote, of Guioa, of *Davallia*, of Terminalia, of Barringtonia, of Trema, of antirobia, cecropia, argania, dioscoreae such as *Dioscorea opposita* or Mexican, extracts of *Ammi visnaga*, of *Siegesbeckia*, in particular *Siegesbeckia orientalis*, vegetable extracts of the family of Ericaceae, in particular bilberry extracts (*Vaccinium angustifollium*) or *Arctostaphylos uva ursi*, aloe vera, plant containing sterols (e.g., phytosterol), Manjistha (extracted from plants of the genus *Rubia*, particularly *Rubia Cordifolia*), and Guggal (extracted from plants of the genus *Commiphora*, particularly *Commiphora Mukul*), kola extract, chamomile, red clover extract, *Piper methysticum* extract (Kava Kava™ from SEDERMA), *Bacopa monieri* extract (Bacocalmine™ from SEDERMA) and sea whip extract, extracts of *Glycyrrhiza glabra*, of mulberry, of melaleuca (tea tree), of *Larrea divaricata*, of *Rabdosia rubescens*, of *Euglena gracilis*, of *Fibraurea recisa Hirudinea*, of *Chaparral Sorghum*, of sun flower extract, of *Enantia chlorantha*, of Mitracarpe of *Spermacocea* genus, of *Buchu barosma*, of *Lawsonia inermis* L., of *Adiantium Capillus-Veneris* L., of *Chelidonium majus*, of *Luffa* cylindrica, of Japanese Mandarin (Citrus reticulata Blanco var. *unshiu*), of Camelia sinensis, of *Imperata cylindrica*, of *Glaucium Flavum*, of *Cupressus Sempervirens*, of Polygonatum multiflorum, of loveylyhemsleya, of *Sambucus Nigra*, of *Phaseolus lunatus*, of Centaurium, of *Macrocystis Pyrifera*, of *Turnera Diffusa*, of *Anemarrhena asphodeloides*, of *Portulaca pilosa*, of *Humulus lupulus*, of *Coffea Arabica* or of *Ilex Paraguariensis*.

The compositions of the present invention may include peptides, including, without limitation, the di-, tri-, tetra-, penta- and hexapeptides and their derivatives. According to a particular embodiment, the concentration of the additional peptide, in the composition, ranges from $1 \times 10^{-7}$% and 20%, preferably from $1 \times 10^{-6}$% and 10%, preferably between $1 \times 10^{-5}$% and 5% by weight. According to the present invention, the term "peptide" refers to peptides containing 10 amino acids or less, their derivatives, isomers and complexes with other species such as a metal ion (eg copper, zinc, manganese, magnesium, and others). The term "peptides" refers to both natural peptides and synthetic peptides. It also refers to compositions that contain peptides which are found in nature, and/or are commercially available.

Suitable dipeptides for use herein include but are not limited to carnosine (beta-AH), YR, VW, NF, DF, KT, KC, CK, KP, KK or TT. Suitable tripeptides for use herein include, but are not limited to RKR, HGG, GHK, GKH, GGH, GHG, KFK, GKH, KPK, KMOK, KMO2K or KAvaK. Suitable tetrapeptides for use herein include but are not limited to RSRK (SEQ ID NO: 5), GQPR (SEQ ID NO: 6) or KTFK (SEQ ID NO: 7). Suitable pentapeptides include, but are not limited to KTTKS (SEQ ID NO: 4). Suitable hexapeptides include but are not limited to GKTTKS (SEQ ID NO: 8), VGVAPG (SEQ ID NO: 9).

Other suitable peptides for use herein include, but are not limited to lipophilic derivatives of peptides, preferably palmitoyl derivatives, and metal complexes as aforementioned (e.g. copper complex of the tripeptide HGG). Preferred dipeptide derivatives include N-Palmitoyl-beta-Ala-His, N-Acetyl-Tyr-Arg-hexadecylester (CALMOSENSINE™ from Sederma). Preferred tripeptide derivatives include N-Palmitoyl-Gly-Lys-His, (Pal-GKH from Sederma), the copper derivative of HGG (Lamin™ from Sigma), Lipospondin (N-Elaidoyl-KFK) and its analogs of conservative substitution, N-Acetyl-RKR-NH$_2$ (Peptide CK+), N-Biot-GHK (from Sederma), Pal-KMO$_2$K (Sederma) and derivatives thereof. Suitable tetrapeptide derivatives for use according to the present invention include, but are not limited to, N-palmitoyl-GQPR (SEQ ID NO: 3) (from Sederma), suitable pentapeptide derivatives for use herein include, but are not limited to, N-Palmitoyl-KTTKS (SEQ ID NO: 2) (available as MATRIXYL™ from Sederma), N-Palmitoyl-Tyr-Gly-Gly-Phe-X (SEQ ID NO: 10) with X Met or Leu or mixtures thereof. Suitable hexapeptide derivatives for use herein include, but are not limited to, N-Palmitoyl-VGVAPG (SEQ ID NO: 1) and derivatives thereof. The mixture of Pal-GHK and Pal-GQPR (SEQ ID NO: 3) (Matrixyl™ 3000, Sederma) can also be mentioned.

The preferred compositions commercially available containing a tripeptide or a derivative include Biopeptide-CL™, Maxilip™, Biobustyl™ and MATRIXYL™ synthe' 6™ of Sederma. The compositions commercially available preferred sources of tetrapeptides include RIGIN™ EYELISS™, MATRIXYLT™ RELOADED and MATRIXYL 3000™ which contain between 50 and 500 ppm of Palmitoyl-GQPR (SEQ ID NO: 3) and carrier, proposed by Sederma.

The following marketed peptides can be mentioned as well as additional active ingredients: Vialox™, Syn-ake™ or Syn-Coll™ (Pentapharm), Hydroxyprolisilane CN™ (Exsymol), Argireline™, Leuphasyl™, Aldenine™, Trylgen™, Eyeseryl™, Serilesine™ or Decorinyl™ (Lipotec), Collaxyl™ or Quintescine™ (Vincience), BONT-L-Peptide™ (Infinitec Activos), CytokinolTMLS (Laboratoires Serobiologiques/Cognis), Kollaren™, IP2000™ or Meliprene™ (Institut Européen de Biologie Cellulaire), Neutrazen™ (Innovations), ECM-Protect™ (Atrium Innovations), Timp-Peptide™ or ECM Moduline™ (lnfinitec Activos).

Cosmetic Treatment Method

The present invention also concerns a cosmetic treatment method to improve the general condition of the skin, comprising the topical application to the skin and/or the appendages of an effective amount of an extract of *Globularia* as recited above.

The extract of *Globularia* for the invention may be applied locally onto areas of the face, lips, neck, neckline, hands, feet, or body. One of the major advantages of the present invention resides in the ability whenever necessary or desirable to be able to apply local selective "gentle" treatments through this topical, non-invasive method of application. In the case of anti-wrinkle use for example it may be applied very locally using a syringe or micro-canula.

It is also possible, however, to consider a composition containing the extract according to the invention intended to be injected subcutaneously.

According to other specific features the cosmetic treatment method according to the invention can be combined with one or more other treatment methods targeting the skin such as lumino-therapy, heat or aromatherapy treatments.

According to the invention, devices with several compartments or kits may be proposed to apply the method described above which may include for example and non-restrictively, a first compartment containing a composition comprising the extract of *Globularia*, and in a second compartment a composition containing another active ingredient and/or excipient, the compositions contained in the said first and second compartments in this case being considered to be a combination composition for simultaneous, separate or stepwise use in time, particularly in one of the treatment methods recited above.

The treatment method of the invention is particularly suited to prevent and/or treat skin aging by stimulating the detoxification reactions and/or cell regeneration through a hormetic type response, in particular for improving the radiance and/or transparency of the skin, for preventing and/or treating sensitive and/or reactive skins, for preventing and/or treating rednesses and/or preventing glycation of proteins.

The treatment method of the invention is also particularly suited for increasing and/or maintaining the number of dermal stem cells, and/or for increasing and/or maintaining the dermal macromolecules, in particular collagen and elastin, and/or for thus increasing the volume of the dermis (replumping), and/or for preventing and/or treating fines lines and wrinkles, and/or for firming skin, and/or for preventing hair loss and/or stimulation hair regrowth.

A) Example of Obtaining an Extract of Plant Origin According to the Invention by Undifferentiated Cell Culture of *Globularia cordifolia*

1) Creation of a Cell Line

*Globularia cordifolia* plants were obtained from seeds.

Leaves are collected, and thereafter cleaned and rinsed with water, and decontaminated and further rinsed.

a) Step of Induction of Undifferentiated Cells or Callus

Pieces of leaves are cut and placed on the surface of a nutrient agar, containing an assimilable carbon source, a solution of micro and macro-elements and a combination of adapted hormones and vitamins. This nutrient medium, thanks to its composition, will trigger the production of clusters of undifferentiated cells called callus at the site of healing of the leaf. Composition of the solid nutrient medium used (according to Gamborg): solution of macro-elements and micro-elements, saccharose, agar plant, plant hormones and vitamins.

pH is Adjusted Between 5.5 and 6.

This medium will be thereafter referred to the "basic medium". This induction step lasts 1 to 4 months. Culture is made at 25° C. in the dark.

b) Stabilization and Selection Step of the Cultures in Agar Medium.

Callus stabilization is obtained after successive transplantations, every 3 weeks, on fresh medium. Stable and homogeneous cultures are thus obtained thanks to their phenotypic characteristics (color, friability, proliferation).

The selection is to choose the best callus cultures for the transfer in liquid medium, among the tens initiated earlier. The selected lines are characterized by high growth, a soft and crumbly texture, uniform color, good dispersion in liquid medium and stability of these parameters during the subcultures.

This step lasts from 6 months to 1 year.

c) Transfer in Liquid Medium and Optimization of the Production of Secondary Metabolites The selected lines are transferred in liquid medium in order to optimize in an initial stage their growth parameters.

Cell growth and appreciation of the different phases (latence, exponential, stationary) are assessed by regular measurement of the percentage volume occupied by the culture cells or "packed cell volume" (PCV).

Different suspensions from the callus are placed on an orbital shaker, agitated at 110 rpm in the dark at 25° C. (in Erlenmeyer flasks each containing 100 ml of medium and 10 grams homogeneous texture, color and growth callus). Several media and hormone combinations are tested and compared in order to optimize the growth curve. The optimization of the initial density of the inoculum is also sought for reducing the lag phase and thus the global duration of culture. Furthermore, the selected initial density for the inoculum corresponds to a PCV of 10%.

The next step is to determine the optimal environmental conditions to direct the cellular metabolism toward the production of secondary metabolites at the end of the growth phase of the culture. These secondary metabolites and the other components of the extract medium as well, will participate in the activity of the extract obtained at the end.

Thus, in the medium, a high proportion of polar molecules were identified, including sugars, amino acids, primary metabolites, cinnamic acid and caffeic derivatives, and mixture of phenylethanoid glycosides. The phenylethanoid glycosides were chosen as indicators of secondary metabolites biomass production, their total dosage being easily achieved by the method of Arnow, a spectrophotometric method based on the oxidation of total polyphenols in alkaline medium by sodium nitrite and sodium molybdate (reading at 510 nm). Other classes of molecules are assumed to be present in the medium, such as flavonoids or iridoids but could not be identified. It is obvious that all of these molecules will be responsible for the activity of the final extract. The elicitation chosen according to the invention to lead to the production of secondary metabolites is then to place the cells in medium depleted of sucrose and macronutrients, preferably in the same proportions.

This transfer phase in liquid medium and optimization of the parameters of growth and production can last from 6 months to 1 year.

After this step, a line giving the best results was selected.

It was subjected to a deposit with DSMZ (Deutsche Sammlung von Mikroorganismen und Zellkuturen GmbH) under the reference DSM25009.

The present invention covers an extract of *Globularia Cordifolia* species obtained from the cell line recorded under the number DSM25009.

2) Extract Obtaining a) Production of Pre-Cultures in Bioreactors

Successive pre-cultures of the cell line selected of 1-liter, then 5 liter, and then 25 liter and finally 100 liter are realized. Each is seeded at 10% PCV and then grown to 50% of PCV. The cell biomass thus produced is used to inoculate the larger size culture. This stage can last from 1 to 3 months.

b) Transfer to Bioreactor Comprising the Elicitation Phase

A single use bag bioreactor (600 liters of total volume and 300 liters of total culture volume) is then seeded between 5 and 20% PVC.

The bioreactor is in particular equipped with:

A rocker system for cell agitation and oxygenation, and for culture temperature regulation, preferably selected because being more suitable with regard to the fragility of plant cells compare to shearing of a conventional bioreactor;

A control tower equipped with different sensors (oxygen, pH and temperature) for the follow-up and the regulation of the culture steps;

A single-use sterile bag for the cell culture, equipped with different sensors (pH, oxygen), a filter for gas supply and exchange systems for sampling or inoculating sterile fluids.

After 10-15 days of culture in the bioreactor, the culture reaches a PCV of about 30 to 45%. The deficient medium is then added to trigger the production of secondary metabolites, including here phenylethanoid glycosides. The addition of fresh medium is 10 to 50% of the final culture volume. After 3-5 days, the culture was stopped at 35-50% of PCV, the phenylethanoid glycosides then being around 2 grams per liter in the culture.

This entire phase in bioreactor lasts 2 to 3 weeks.

c) Recovery of the Extract

The aim of this subsequent step is to produce an aqueous and clarified extract.

A cell lysis is achieved, leading to the release of secondary metabolites in the liquid phase. This lysis is carried out by acidification. A cascade filtration is then carried out, the first in-depth, followed by sterile filtration, to obtain the aqueous extract of the invention. This step is intended to stabilize the extract.

The extract obtained this way by plant cell culture is clear, colorless to pale yellow, to the contrary of the "classic" plant extract which is bright yellow, which is an advantage for a direct subsequent formulation of the extract in a cosmetic ingredient or other.

Variants of this Process Exist, Including:

1) For the extraction of the molecules of interest:

The cell lysis step can be performed by biomass thermal treatment, for example by injecting steam into the biomass. It can also be made by grinding the cells with microbeads.

After the cell lysis step, it is possible to purify the crude extract, in order to enrich it in molecules of interest. According to this, biomass is first removed by filtration or centrifugation. The resulting clarified liquid phase is then contacted with an adsorbent resin, selected for its affinity with the molecules of interest. This resin is then loaded into a glass chromatography column. The resin is eluted with appropriate mixtures and the elution of the product concentrated.

The recovery of the extract according to the invention can be implemented using liposomes.

2) Regarding the elicitation mode of the molecules of interest:

The elicitation of compounds of interest can also be done by adding microbial fractions to the culture, by adding molecules of biological origin such as, chitosan, methyljasmonate, jasmonic acid, salicylic acid, by adding molecules of non-biological origin such as paclobutrazol, by applying to the culture a temperature variation, a pH variation, and/or an osmotic stress induced by a non-metabolizable sugar, such as mannitol, by using an even more drastic impoverishment of the environment in macro-elements and sugar, by adding to the culture adsorbent resins that in addition to elicitation of the compounds of interest production can trap them.

3) Instead of the cell line creation stage, a cell line according to the invention already prepared and preserved can be used. In this case, the step of creating the cell line is replaced by a conventional step of amplification of undifferentiated plant cells from said cell line existing first in agar and in liquid medium.

The invention method could also be achieved with the other species of *Globularia*.

B) Example of Formulation of a Composition for Implementing the Invention which is an "Active Ingredient", a Raw Material for the Cosmetics Industry The active ingredient is a cosmetic composition containing the extract of plant origin of *Globularia* cordifolia dissolved in a dermatologically acceptable medium or matrix. This active ingredient is intended for the cosmetics industry for the preparation of cosmetics, such as creams, gels, etc. (see galenic examples given below).

The aqueous extract obtained in Example A) above may preferably be mixed at 20 to 80% with any hydrophilic matrix as a gel, an aqueous buffer, glycerin or other short-chain polyol physiologically acceptable.

For example, and for the achievement of the studies and galenic presented thereafter, an extract up to 33% was preferentially used.

Of course, a pure extract without excipient can also be used as the active ingredient.

C) In Vitro and Ex-Vivo Studies

The applicants have demonstrated a number of remarkable cosmetic effects of the *Globularia* extract which are presented below.

An aqueous extract prepared according to Example B) above, up to 33%, was tested in vitro and showed various cosmetic activities, concerning several areas of the skin physiology. The tests were all performed with 2% of such *Globularia cordifolia* extract.

Comparative Tests

First, the superiority of the extract obtained by cell culture versus a hydroalcoholic extract of the whole plant has been shown. These first tests were carried out by comparing an aqueous extract prepared according to Example B) above, up to 33%, diluted to 2%, compared to the hydroalcoholic extract of whole plant at an equivalent concentration in phenylethanoid glycosides.

1) Non-Enzymatic Glycation of BSA

This simple test reproduces in vitro a stress to which regular skin proteins are subjected: their functional alteration by a non-enzymatic glycation phenomenon.

The study model used is a bovine serum albumin (BSA), which is contacted with a physiological reducing sugar, the fructose, giving a spontaneous and slow reaction between the two molecules that can be accelerated by temperature. In this test, the BSA and fructose are incubated in the presence or absence of the test products at 50° C. for 7 days. The glycation end products have a natural fluorescence that can be quantified using a fluorimeter ($\lambda$ex=360 nm and $\lambda$em=460 nm). 0.03% Aminoguanidine is used as a positive control of glycation inhibition. Data are given in Table 1 below.

TABLE 1

| Glycation inhibition | % Change vs. control |
|---|---|
| *Globularia cordifolia* hydroalcoholic plant extract | +8% (dns*) |
| *Globularia cordifolia* cell culture extract | −64% (p < 0.01) |

*dns = non-significant data

The positive control has a glycation inhibition of −85% versus the control.

2) DPPH Anti-Radical Test

The DPPH (1,1-diphenyl-2-picryl hydrazyl) is a stable free radical which is widely used for the detection of free radical scavengers. This molecule by losing its radical character is converted to DPPH2 (1,1-diphenyl-2-picryl hydrazine). This conversion is accompanied by discoloration (purple→yellow) which can be monitored over time by spectrophotometry at 517 nm. Control with no antiradical activity keeps a constant DO. 0003% of caffeic acid is used as a positive control for anti-radical activity. Data are given in Table 2 thereafter.

TABLE 2

| Anti-radical activity | % Change vs. control |
|---|---|
| *Globularia cordifolia* hydroalcoholic plant extract | −1% (dns) |
| *Globularia cordifolia* cell culture extract | +53% (p < 0.01) |

The positive control has an anti-radical activity of −85% versus the control.

3) Anti-Singlet-Oxygen Test

Molecular oxygen ($O_2$) plays a vital role as an acceptor of the respiratory chain terminal electrons. However, this metabolism and others, as well as external factors, such as UV radiations, lead to the occurrence of certain derivatives particularly reactive (singlet oxygen, hydroxyl radical, superoxide anion), which will cause oxidative damage to lipids, proteins and nucleic acids, even in healthy bodies. Singlet oxygen is one of these very energetic and highly reactive forms of oxygen. It is possible to produce experimentally in vitro singlet oxygen with dyes and UVA photons or visible light. The test presented thereafter uses the Rose Bengal, a dye and visible light. The purpose of this test is to evaluate the degradation of uric acid by singlet oxygen formed from the Rose Bengal, under the action of visible light. The visualization of the production of singlet oxygen is obtained by following the destruction of uric acid at 292 nm. In the presence of a compound capable of neutralizing singlet oxygen, this destruction will be slowed. The caffeic acid at 0002% is used as a positive control of an anti-singlet-oxygen activity Data in Table 3 below.

TABLE 3

| Anti-singlet-oxygen activity | % Change vs. control |
|---|---|
| *Globularia cordifolia* hydroalcoholic plant extract | +14% (dns) |
| *Globularia cordifolia* cell culture extract | +33% (p < 0.01) |

The positive control has an anti-singlet-oxygen activity of +73% versus the control.

These three tests show the cosmetic interest of the *Globularia* extract obtained by cell culture, which also has a much higher efficiency compared to the hydroalcoholic extract obtained from the plant.

Studies on the *Globularia cordifolia* Cell Culture Extract

These studies were carried out with an aqueous extract prepared according to Example B) above, up to 33%, diluted to 2%.

Protection of Keratinocytes in Culture by the Extract of the Invention Facing a Double Stress, Mechanical and Oxidative Confluent keratinocytes layers were put in contact (test) or not (control) with 2% of the extract of the invention to in a culture medium for 24 hours. The layers were then "wounded" in a reproducible manner and after immediately exposed to UVB to assess their ability to resist to two stresses commonly suffered by the skin. The recovery of cell layers was then evaluated by image analysis, by quantifying the surface free of cells (results in Table 4 below).

TABLE 4

|  |  | Scar surface (in arbitrary units) | | Wound surface % recolonized |
|---|---|---|---|---|
|  |  | T0 | T48 hours | at T48 hours |
| Keratinocytes; n = 9 | Control | 43.3 +/− 7.1 | 19.8 +/− 11.3 | 54.3% |
|  | *Globularia cordifolia* extract | 40.4 +/− 9 | 2.9 +/− 6.6 | 92.8% |

The visual observations showed that the control layers underwent a profound alteration of their integrity (with some cell death) and had a great difficulty to recolonize the injured surface. To the contrary, the layers that were in contact with the *Globularia cordifolia* plant cell extract were less altered and re-form faster a dense and uniform layer.

This preliminary test illustrates well the hormetic phenomenon at work in the presence of the extract of *Globularia*. Presumably, the cells pre-contact with the extract resulted in the establishment of a number of lines of defense, including antioxidant, before stress, then used by the cells to counteract the deleterious effects of stress and regenerate a normal cell layer.

This hormetic effect of the *Globularia cordifolia* extract has been in vitro demonstrated and quantified by studying the following three distinct axes (4-6).

4—Preservation of Epidermal Progenitors

Principle

The epidermis regenerates continuously in order to produce an effective skin barrier. This effect declines with age. The cells at the start of this process are called stem cells or progenitor cells. They are rare but keep their potential to regenerate because of the quality of their molecular links binding them to their immediate environment.

Harmful treatments such as oxidants alter the environment of these cells and make them evolve into a different phenotype, causing a change in their subsequent ability to proliferate. In vitro these cells, having lost their proliferative capacity, form small colonies, which may be invisible to the naked eye, the daughter cells in these colonies being relatively large. To the contrary, progenitor cells can multiply extensively in order to regenerate the skin and produce larger colonies with smaller cells. This potential for regeneration and therefore progenitor cell density in a culture is measured by the cloning efficacy method. This method involves counting the number of colonies visible to the naked eye after seeding cells at low density and culturing for a specific time. The number obtained is used as a measure of the progenitor vigor of the initial cell population.

Confluent human epidermal progenitor keratinocytes were placed in contact with an optimum medium to force their conversion into differentiated keratinocytes (so to make them lose their progenitor phenotype) in the presence or absence of the *Globularia cordifolia* extract. Following the contact, the cells of the two series were reseeded at a concentration of 1000 cells/25 cm2 (n=5) into the differentiating medium.

Results

After culturing for 12 days, the number and size of the colonies can be measured after fixation and staining. The results show that the control cases presented 5.4±1.5 colonies/1000 seeded cells and that the colonies were small in size. In parallel, contact with the *Globularia cordifolia* extract gave 2.3 times more colonies (12.6 colonies±4.3 colonies/1000 seeded cells; +133%; p<0.01) than the control and the colonies were larger in size.

This shows that the *Globularia cordifolia* extract prevents progenitor cells from converting to a differentiated stage and maintains their proliferative capacity. It preserves according to this the epidermal capacity to regenerate itself.

5—Stimulation of the Energetic Potential a. Sirtuin 1

Hormetic effects such as calorie restriction or contact with hormetic molecules increase sirtuin enzymes and the lifespan of different organisms. The sirtuins act particularly on FOXO factor deacetylation and prevent triggering of the production of apoptotic proteins. The sirtuins also stimulate cellular anti-oxidant defenses and purification mechanisms (detoxification) and help to preserve mitochondrial function and therefore energy production. This increases survival and resistance to stresses.

Human keratinocytes were cultured in the presence or absence of the *Globularia cordifolia* extract for 6 days and were then grinded and the intracellular levels of sirtuin-1 were measured using an ELISA method. Results were standardized by parallel measurement of total protein (BCA). Results are given below in Table 5.

TABLE 5

|  |  | Sirtuin-1 (ng/mg of protein) | % Change; significance |
|---|---|---|---|
| Keratinocytes; n = 5 | Control | 2.10 ± 0.58 | Reference |
|  | *Globularia cordifolia* extract | 3.65 ± 0.33 | +74%; p < 0.01 |

Positive control Trolox at 500 μm: +27%; p<0.05.

In parallel, abdominal skin explants (58 years female) received a topical application daily for 6 days of a cream containing the *Globularia cordifolia* extract of the invention or its placebo (ex vivo test). After this treatment, the explants were prepared and labeled with fluorescent antibodies to quantify sirtuin-1. This quantification uses an image analysis system after photography (50 photos/per case). The results are given in Table 6 thereafter.

TABLE 6

|  |  | Sirtuin-1 (Intensity of fluorescence). | % Change; significance |
|---|---|---|---|
| Skin explants; n = 5 | Placebo | 10.94 ± 2.40 | Reference |
|  | *Globularia cordifolia* extract | 12.23 ± 2.80 | +12%; p < 0.03 | b. Creatine Kinase

Creatine kinase is a ubiquitous enzyme which exists in two isoforms in the skin. It is used to store energy in cells and enables tissues to respond to urgent energy requirements. This enzyme converts creatine into phosphocreatine using ATP which is converted back to ADP. When necessary, the enzyme works in the reverse direction and returns energy. Its activity falls with age as it is one of the preferred targets of reactive oxygen groups. Maintaining and increasing the activity of this enzyme is therefore desirable.

Human dermal fibroblasts were placed in contact with the *Globularia cordifolia* extract according to the invention for 3 days. The cells were then exposed without said extract to an oxidative stress (hydrogen peroxide). After a further 3 days' contact with the *Globularia cordifolia* extract, the cells were again exposed to the same oxidative stress before being homogenized to measure residual intracellular creatine kinase activity. Activity was measured from the production of ATP from phosphocreatine and ADP. ATP is then measured from an enzymatic reaction leading to the formation of NADPH, readed at 340 nm. Results were standardized by measuring total protein (BCA). Results are given below in Table 7.

TABLE 7

| | | Creatin kinase activity (U/mg protein) | % Change; significance | |
|---|---|---|---|---|
| Fibroblasts; n = 5 | Control without $H_2O_2$ | 0.307 ± 0.020 | Reference 1 | — |
| | Control with $H_2O_2$ | 0.247 ± 0.030 | −19%; p < 0.02 | Reference 2 |
| | $H_2O_2$ and Globularia cordifolia extract | 0.381 ± 0.055 | — | +54%; p < 0.01 |

Positive control Trolox at 500 µm: +28%; p<0.05.

The explants already used for Sirtuin-1 were labeled with fluorescent antibody to assess the amount of mitochondrial epidermal creatine kinase. Quantification was performed using an image analysis system after taking photos (50 photos/per case). The results are given in Table 8 thereafter

TABLE 8

| | | Mitochondrial creatine kinase (Intensity of fluorescence). | % Change; significance |
|---|---|---|---|
| Explants; n = 5 | Placebo | 7.62 ± 1.70 | Reference |
| | Globularia cordifolia extract | 10.81 ± 2.30 | +42%; p < 0.01 | c. Mitochondrial Membrane Potential

The mitochondrion is a major site involved in the formation of reactive oxygen groups which, over time, interfere with the functioning of its respiratory chain. This causes a decrease in mitochondrial membrane potential ($\Delta\Psi$), causing a reduction of the ATP production.

A fall in this membrane potential is a warning sign of ageing and cell death and it is therefore essential that this be maintained to preserve the mitochondrial ability to produce ATP.

Membrane potential was measured using a specific label sensitive to mitochondrial proton micro-variations. The label exists in two forms, monomeric and polymeric, which have different emission spectra. A high membrane potential promotes the polymeric form. An increase in the monomer/polymer ratio (520 nm/590 nm) produces therefore a fall in $\Delta\Psi$.

A high ratio is therefore less conducive to cell survival than a lower ratio.

The same fibroblast cultures than used for creatine kinase there above were used. The results are given below in Table 9.

TABLE 9

| | | Ratio | % Change*; significance | |
|---|---|---|---|---|
| Fibroblasts; n = 5 | Control without $H_2O_2$ | 6.15 ± 1.33 | Reference 1 | — |
| | Control with $H_2O_2$ | 8.13 ± 1.12 | −32%; p < 0.01 | Reference 2 |
| | $H_2O_2$ and Globularia cordifolia extract | 4.89 ± 0.57 | — | +40%; p < 0.01 |

*% Change = 100 × [(Control − Globularia cordifolia extract/Control]

Positive control Trolox at 500 µm: +36%; p<0.05.

Membrane potential therefore improved very markedly with the Globularia cordifolia extract of the invention (+40%, p<0.01).

This study complements the two previous studies to demonstrate the ability of the Globularia cordifolia extract of the invention for anti-aging prevention. It stimulates spontaneously the amount of sirtuin1. It maintains the activity of creatine kinase and protects the production of ATP in response to an oxidative stress.

6—Combatting Noxious Products a. Endogenous Peroxides

One of the indicators traditionally used to assess the vitality of a cell population is the level of oxidative stress.

This factor can be measured reliably using a probe called DCFH-DA, whose characteristic is to fluoresce in contact with peroxides once it entered the cell.

Protocol

Confluence human keratinocytes were placed in contact or not (negative control) for 24 h with the Globularia cordifolia extract until they grew to confluence. The cells were then exposed to and metabolized the DCFH label in a buffer. The label can then react with both intracellular peroxides. The medium was then replaced with one containing or not the Globularia cordifolia extract and the oxidizing agent model hydrogen peroxide (neither the medium nor the Globularia cordifolia extract reacts directly with $H_2O_2$). Fluorescence was read in order to estimate the level of the intracellular peroxide which had reacted with the label. The number of cells was quantified using a nuclear labeling method (Hoechst 33258). The results are given below in Table 10.

TABLE 10

|  |  | Intracellular peroxide (UFA/10³ cells) | % Change; significance | |
|---|---|---|---|---|
| Kerati-nocytes; n = 5 | Non peroxidized control | 37.3 ± 2.2 | Reference 1 | — |
| | Negative control with H₂O₂ | 1099 ± 24.0 | X29; p < 0.01 | Reference 2 |
| | H₂O₂ and Globularia cordifolia extract | 137 +/− 4.0 | — | −88%; p < 0.01 |

AFU: Arbitrary fluorescence units; Positive control Trolox 500 µm: −91%; (p<0.01). The *Globularia cordifolia* extract according to the invention protects intracellular content from the rise in peroxides induced by hydrogen peroxide. This result reflects a reduction of the damage generated by free radicals or reactive oxygen species following oxidative stress in the presence of the *Globularia cordifolia* extract.

b. SOD and Catalase

Antioxidant enzymes such as catalase or SOD, produced by our bodies, as well as antioxidants, vitamins E and C, carotenoids, etc. which are drawn from our food, help to fight against the harmful effects of free radicals and reactive oxygenated species. So there is a clear interest in increasing their number by stimulating their synthesis.

A preliminary test on the antioxidant skin potential had shown that human keratinocytes treated with the hydrogen peroxide, a model of oxidative stress, increased their intracellular activity of SOD (superoxide dismutase) by 22% *(p<0.01) compared to the negative control in the presence of the *Globularia cordifolia* extract.

*Positive control Trolox at 0.012%: SOD 21%; p<0.01.

In addition, explants of abdominal skin (woman, 58 years) received 1 topical application daily for 6 days of a cream containing the *Globularia cordifolia* extract or its placebo.

At the end of this treatment, the explants were prepared and labeled with anti-SOD fluorescent antibody on the one hand or anti-catalase on the other. Quantification was performed using an image analysis system after taking photos (50 photos/case). The results are given in Tables 11 and 12 below.

TABLE 11

|  |  | SOD (Intensity of fluorescence) | % Change; significance |
|---|---|---|---|
| Skin explants; n = 5 | Placebo | 6.31 ± 2.00 | Reference |
| | Globularia cordifolia extract | 8.58 ± 1.40 | +36%; p < 0.01 |

TABLE 12

|  |  | Catalase (Intensity of fluorescence). | % Change; significance |
|---|---|---|---|
| Skin explants; n = 5 | Placebo | 6.87 ± 2.90 | Reference |
| | Globularia cordifolia extract | 12.24 ± 3.70 | +78% p < 0.01 |

The *Globularia cordifolia* therefore stimulates SOD and catalase production, independently of any stress. These "spontaneous" stimulation, found in Hormesis, enable the skin to prepare appropriate defenses against stresses which may occur later.

c. Proteasome and Glycation

Proteins which are damaged by glycation, oxidation (carbonylated proteins) or conjugation with lipid peroxides tend to accumulate in the cell during ageing. They are removed routinely by the proteasome which reduces their harmful effect on cellular homeostasis. The activity of the proteasome, however, is reduced by these accumulations, and by accumulation of lipofuscin, a lipoprotein waste product, or in time, leading to further increased amounts of damaged proteins by a vicious cycle.

Maintaining the activity of the proteasome is one of the beneficial consequences of hormesis as it supplements the cells anti-ageing defense armamentarium. It helps to remove waste which accumulated in the cell, leading to the production of pre-inflammatory substances which opacify the cells.

Human dermal fibroblasts were placed or not (negative control) in contact with the *Globularia cordifolia* extract until they grew to confluence. The *Globularia cordifolia* extract was then removed and the cells were exposed to the oxidant model, hydrogen peroxide, to produce accelerated ageing. After this stage, the cells were again exposed to the *Globularia cordifolia* extract for 3 days and then were reseeded and subjected to a further oxidative stress to amplify the effect of the initial stress.

The cells were then homogenized and the residual proteasome activity measured by monitoring cleavage of a model fluorescent peptide. Results were standardized by parallel measurement of protein. Results are given thereafter in Table 13.

TABLE 13

|  |  | proteasome activity (UFA/µg proteins) | % Change; significance | |
|---|---|---|---|---|
| Fibroblasts; n = 5 | Non peroxidized control | 1.138 ± 0.15 | Reference 1 | — |
| | Control with H₂O₂ | 0.342 ± 0.04 | −70%; p < 0.01 | Reference 2 |
| | H₂O₂ and Globularia cordifolia extract | 0.538 +/− 0.11 | — | +57%; p < 0.01 |

AFU: Arbitrary fluorescence units; Positive control Trolox 500 µm: +24%; (p<0.05).

The anti-glycation effect of the extract of *Globularia cordifolia* was studied using a protein model, BSA and a natural reducing sugar, fructose which glycates, i.e. binds, to the protein in a non-enzymatic manner. The product of this binding is fluorescent and is monitored with a recording system. Results are given below in Table 14.

TABLE 14

|  |  | Glycation (Intensity of fluorescence) | % Change; significance |
|---|---|---|---|
| Protein BSA model; n = 4 | Control | 21206 +/- 140 | Reference |
|  | *Globularia cordifolia* extract | 7668 +/- 121 | -64%; p < 0.01 |

Positive control aminoguanidine at 0.03%: -85%; p<0.01.

d) Glutathion

In addition to its well-known antioxidant role, glutathion is the most important detoxification element of the body and the principal agent of the good health of the body. It binds to toxins such as heavy metals, solvents and pesticides, and transforms them into water-soluble compounds that can easily be eliminated in bile or urine.

Glutathion synthesis was spontaneously stimulated in keratinocytes in the presence of the cell culture extract of *Globularia cordifolia*: +49%*(p<0.01) compared to the negative control who did not receive the extract.

*Positive control Trolox at 0.012%: GSH: 53% (p<0.01)

The hormetic type effect ("hormesis-like") of the extract according to the invention has thus been shown in particular in 3 directions:

A direct strengthening of the molecules and metabolite pathways that contribute the cells to be more responsive to an ulterior stress (sirtuins, SOD, catalase, glutathion);

By direct protection of the energy potential of the cell and its integrity against oxidative stress (creatine kinase, mitochondrial potential, proteasome, level of peroxides or glycated proteins) and—

By maintaining the skin regenerative capacity, promoting the progenitor phenotype and therefore proliferative in cells in charge of this function.

Studies on Dermal Stem Cells

These studies were carried out with an aqueous extract prepared according to Example B) above, up to 33%, diluted to 1%, 2% or 3%.

As study model, dermal stem cells from the follicular dermal papilla were used (HFDPC). They were drop seeded to make a "Hanging drop" type culture, in the presence or absence of the *Globularia cordifolia* extract (n=43 drops/box).

The maintaining of the phenotype of stem cells in the dermal papilla through the Sphere-forming properties and specific markers, Nestin and SOX2, has been studied.

Sphere Forming Properties

The capacity of cells to in three dimensional spheres is a characteristic of dermal stem cells phenotype. The loss of this phenotype figures differentiation of these cells and the remoteness of stem feature. When a culture shows a greater number of spheres that another, it means it is richer in skin stem cells.

The cells are left in contact with the extract for the time for the spheres to be formed. After adhesion of the spheres, their number is counted. The results are presented in Table 15 below.

TABLE 15 n = 9 photos/box on n = 3 boxes

|  |  | Mean sphere number/fields | % Change vs control |
|---|---|---|---|
| Control |  | 1.33 +/- 0.71 | Reference |
| *Globularia cordifolia* extract | 1% | 3.67 +/- 1.58 | +175%; p < 0.01 |
|  | 2% | 2.89 +/- 1.17 | +117%; p < 0.01 |
|  | 3% | 4.33 +/- 2.78 | +225%; p < 0.01 |

A significant increase of the number of sphere in the presence of the *Globularia cordifolia* extract is observed compared to the non-treated control.

Specific Labeling

Immunolabeling of the SOX2 and Nestin expression, specific markers of stem cells, is performed and evaluated. The results are given in Tables 16 and 17 below.

TABLE 16 n = 15 photos/box on n = 3 boxes

|  |  | SOX2 (UFA) | SOX2 % change vs control |
|---|---|---|---|
| Control |  | 0.2 +/- 0.35 | Reference |
| *Globularia cordifolia* extract | 2% | 1.01 +/- 1.27 | +339%; p < 0.01 |
|  | 3% | 4.1 +/- 3.54 | +1676%; p < 0.01 |

TABLE 17 n = 15 photos/box on n = 3 boxes

|  |  | Nestin (UFA) | Nestin % change vs control |
|---|---|---|---|
| Control |  | 2.68 +/- 0.94 | Reference |
| *Globularia cordifolia* extract | 1% | 5.64 +/- 2.85 | +110%; p < 0.01 |
|  | 3% | 6.29 +/- 2.35 | +135%; p < 0.01 |

The above results show that the stem phenotype is maintained or preserved thanks to the treatment with the *Globularia cordifolia* extract compared to untreated cells.

D) Galenic

Active Ingredient According to the Invention:

Formula comprising the aqueous extract of *Globularia cordifolia* according to the invention (as disclosed in above example B at 33%).

Different formulas are described below with or without additional cosmetic active ingredients, the latter coming as appropriate to support and/or in addition to the activity of the active ingredient of the invention. These ingredients can be of any class according to their(s) function(s), site of application (body, face, neck, chest, hands, etc.), the desired final effect and the target consumer, such as anti-aging, anti-wrinkle, moisturizing, circles and/or bags under the eyes, firming, brightening, anti-glycation, anti-spots, slimming, soothing, muscle-relaxant, anti-redness, anti-stretch marks, etc.

Example 1: Day Cream Form for Face

| Ingredients | INCI names | % by weight |
|---|---|---|
| Phase A | | |
| H₂O | Water | Qsp100 |
| Ultrez 10 | Carbomer | 0.25 |
| Phase B | | |
| Butylen glycol | Butylene glycol | 2.00 |
| Phenoxyethanol | Phenoxyethanol | qs |
| Phase C | | |
| Brij S2/Volpo S2 | Steareth-2 | 0.40 |
| Brij S10/Volpo S 10 | Steareth-10 | 1.20 |
| Crodafos CES | Cetearyl alcohol & Dicetyl phosphate & Ceteth 10 phosphate | 4.00 |
| Crodacol CS 90 | Cetearyl Alcohol | 1.00 |
| Laurocapram | Azone | 2.50 |
| DC 345 | Cyclohexasiloxane & Cyclopentasiloxane | 2.00 |
| Crodamol OSU | Ethylhexyl succinate | 7.00 |
| Phase D | | |
| Potassium sorbate | Potassium Sorbate | 0.10 |
| Phase E | | |
| H₂O | Water | 3.00 |
| NaOH 30% | Sodium Hydroxide | 0.40 |
| Phase F | | |
| Active ingredient comprising the *Globularia cordifolia* extract | | 2.00 |

Procedure:

Weigh Phase A and let swell without stirring for 30 min. Heat Phase A to 75° C. in a water bath. Weigh and mix Phase B. Weigh Phase C and heat to 75° C. in a water bath. Add Phase B into Phase A. Mix well. Under stirring add Phase C into Phase (A+B). Homogenize well. Add Phase D, extemporaneously. Add Phase E, homogenize well. Add Phase F, mix thoroughly.

Example 2: Gel Form for the Face

| Ingredients | INCI names | % by weight |
|---|---|---|
| Phase A | | |
| H₂O | Water | Qsp 100 |
| Cetyl hydroxyethylcellulose | Cetyl hydroxyethylcellulose | 0.30 |
| Phase B | | |
| Ultrez 10 | Carbomer | 0.40 |
| H₂O | Water | 20.00 |
| Phase C | | |
| Glycerin | Glycerin | 3.00 |
| Panstat | Ethyl & Methyl & Propyl parabens | 0.30 |
| Phase D | | |
| Marcol 82 | Mineral oil | 4.00 |
| Crillet 1 | Polysorbate 20 | 1.00 |
| Crodamol AB | C12-15 Alkyl Benzoate | 2.00 |
| Pemulen TR2 | C10-30 Alkyl Acrylate cross polymer | 0.30 |
| Phase E | | |
| Potassium sorbate | Potassium Sorbate | 0.10 |
| Phase F | | |
| H₂O | Water | 5.00 |
| NaOH 10N | Sodium Hydroxide | 0.50 |
| Phase G | | |
| Active ingredient comprising the extract of *Globularia cordifolia* | | 2.00 |

Procedure:

Disperse Phase A under stirring. Sprinkle Ultrez 10 in water, let stand 30 minutes. Heat Phase C until it is completely dissolved. Mix Phase A with Phase B. Add Phase C in Phase (B+A). Add Phase D under in phase (A+B+C). Add Phase E. Neutralize with Phase F. Add Phase G and mix.

Examples of additional ingredients that can be added to the gel type formula in one of the phases or extemporaneously according to their hydrophobic or hydrophilic physical property at a certain % depending on their concentration and the desired effect:

RIGIN™: active marketed by SEDERMA (WO2000/433417) improving the elasticity and firmness of the skin, increasing hydration and smoothing the skin. 3% by weight of this ingredient may for example be added to the formulation in phase G.

RENOVAGE™: global anti-aging active ingredient marketed by SEDERMA (WO2006/020646). 3% by weight of this ingredient may for example be added to the formulation in Phase D.

LUMISKIN™: active ingredient marketed by SEDERMA (WO2004/024695), which lightens the complexion. 3% by weight of this ingredient may for example be added to the formulation in Phase D.

SUBLISKIN™: active ingredient marketed by SEDERMA (WO2009/055663) that moisturizes and smooths the skin while allowing it to resist to external aggressions. 3% by weight of the ingredient may for example be added to the formulation in phase G.

MATRIXYL 3000™: anti-wrinkle peptide-based active ingredient marketed by SEDERMA (WO2005/048968) which helps to repair skin damages caused by aging. 3% by weight of this ingredient may for example be added to the formulation in phase G.

Example 3: Night Cream Form for Face

| Ingredients | INCI names | % in weight |
|---|---|---|
| Phase A | | |
| H₂O | Water | qsp100 |
| Ultrez 10 | Carbomer | 0.40 |
| Phase B | | |
| Glycerin | Glycerin | 3.00 |
| Panstat | Ethyl & Methyl & Propyl parabens | 0.30 |

-continued

| Ingredients | INCI names | % in weight |
|---|---|---|
| Phase C | | |
| Polawax GP 200 | Cetearyl Alcohol & polysorbate 20 | 1.00 |
| Crodacol CS 90 | Cetearyl Alcohol | 1.00 |
| Crodamol STS | PPG-3 Benzyl Ether Myristate | 1.00 |
| DC 200 5 cps | Dimethicone | 2.50 |
| Crodamol TN | Isotridecyl Isononanoate | 5.00 |
| Phase D | | |
| Potassium sorbate | Potassium sorbate | 0.10 |
| Phase E | | |
| NaOH 30% | Sodium hydroxide | 0.40 |
| H$_2$O | Water | 4.00 |
| Phase F | | |
| Active ingredient comprising the extract of *Globularia cordifolia* | | 2.00 |
| Phase G | | |
| Fragrance | Fragrance | 0.10 |

Procedure:

Weigh Phase A and let swell for 30 minutes. Then heat Phase A in a water bath at 75° C.; heat Phase B until dissolved. Add Phase B to Phase A. Heat Phase C in a water bath at 75° C. Under stirring, add Phase C in Phase (A+B). Add Phase D, homogenize well. Neutralize with Phase E around 55° C. Add Phase F, then Phase G, homogenize well.

Examples of additional ingredients that can be added to the cream type formula in one of the phases or extemporaneously according to their hydrophobic or hydrophilic physical property at a certain % depending on their concentration and the desired effect:

DERMAXYL™: anti-aging active ingredient marketed by SEDERMA (WO2004/101609) which smooths wrinkles and repairs the skin bather. 3% by weight of this ingredient can be added just before use, for example in phase (A+B+C).

Niacinamide (Vitamin B3), Retinol, resveratrol, DHEA: anti-aging ingredients, including anti-wrinkle 0.5% by weight of retinol, resveratrol or DHEA may for example be added extemporaneously to the phase (A+B+C). 10 wt % of Niacinamide 10% in water for example, can be added to the phase G.

Hexamidine: anti-bacterial active that can be added to the G phase of the formulation to 0.5% by mass.

CHRONODYN™: active ingredient marketed by SEDERMA (WO2006/075311) which tones and firms the skin, erases visible signs of fatigue. 3% of this ingredient may for example be added to the phase G.

VENUCEANE™: active ingredient marketed by SEDERMA (WO2002/066668) that prevents visible signs of photo-ageing (spots, wrinkles, dryness, etc.), protects cell structures from damages caused by UV and strengthens skin integrity. 3% of this ingredient may for example be added to the phase G.

Example 4: Cream Form for the Body

| Ingredients | INCI names | % by weight |
|---|---|---|
| Phase A | | |
| H$_2$O | Water | qsp 100 |
| Ultrez 10 | Carbomer | 0.40 |
| Phase B | | |
| Glycerin | Glycerin | 3.00 |
| Panstat | Ethyl & Methyl & Propyl parabens | 0.30 |
| Phase C | | |
| Crill 3 | Sorbitan Stearate | 2.00 |
| Marcol 82 | Mineral oil | 4.00 |
| Cromollient DP3A | PPG 3 Myristyl Ether Adipate | 1.00 |
| Cithrol GMS AS | Glyceryl stearate & PEG 100 stearate | 3.00 |
| Phase D | | |
| Potassium sorbate | Sorbate de potassium | 0.10 |
| Phase E | | |
| NaOH 30% | Sodium hydroxide | 0.40 |
| H$_2$O | Water | 4.00 |
| Phase F | | |
| Active ingredient comprising the extract of *Globularia cordifolia* | | 2.00 |
| Phase G | | |
| Fragrance | Fragrance | 0.10 |

Procedure: Weigh Phase A and let swell for 30 minutes. Heat Phase A in a water bath at 75° C.; heat Phase B until dissolved. Add Phase B to Phase A. Heat Phase C in a water bath at 75° C. Under stirring, add Phase C in Phase (A+B). Add Phase D, homogenize well. Neutralize with Phase E around 55° C. Add Phase F, then Phase G, homogenize well.

Examples of additional ingredients that can be added to the cream type formula in one of the phases or extemporaneously according to their hydrophobic or hydrophilic physical property at a certain % depending on their concentration and the desired effect:

JUVINITY™: active marketed by SEDERMA reducing signs of aging on the face and neckline, smoothing wrinkles, densifying and restructuring the dermis. 2% of this ingredient may for example be added extemporaneously to Phase (A+B+C).

Tocopherol or vitamin E: actives having anti-radical and antioxidant properties.

O.D.A. White™: active marketed by SEDERMA (WO1994/07837) which lightens the skin by reducing the synthesis of melanin. 1% of that ingredient may for example be added extemporaneously to Phase (A+B+C).

Tocopherol (vitamin E) or α-lipoic acid (ALA): active with anti-oxidant and anti-radical properties. 0.5% by weight can be added for example to Phase (A+B+C).

Bio-Bustyl™: active marketed by SEDERMA based on peptide and a bacterial filtrate having a global action on firmness and tone of the bust. 3% of this ingredient can be added for example to Phase G.

Example 5: Serum Form

| Ingredients | INCI names | % by weight |
|---|---|---|
| Phase A | | |
| Optasens G 40 | Carbomer | 0.25 |
| H₂O | Water | Qsp100 |
| Phase B | | |
| Butylene Glycol | Butylene Glycol | 3.00 |
| Phenoxyethanol | Phenoxyethanol | 0.20 |
| Phase C | | |
| Crillet 1 | Polysorbate 20 | 0.50 |
| DC 245 | Cyclopentasiloxane | 1.00 |
| Crodamol CAP | Cetearyl Ethylhexanoate | 2.00 |
| Crodamol STS | PPG-3 Benzyl Ether Myristate | 0.50 |
| Pemulen TR2 | Acrylates/C 10-30 Alkyl Acrylates crosspolymer | 0.20 |
| Phase D | | |
| Potassium sorbate | Potassium Sorbate | 0.10 |
| Phase E | | |
| H₂O | Water | 4.00 |
| NaOH 30% | Sodium Hydroxide | 0.45 |
| Phase F | | |
| Active ingredient comprising the extract of *Globularia cordifolia* | | 2.00 |
| Phase G | | |
| Fragrance | Fragrance | 0.10 |

Procedure:

Phase A: Sprinkle carbomer in water, let swell 15 minutes. Mix Phase B. Pour Phase B in Phase A and homogenize. Weigh Phase C, mix and add in Phase (A+B), under stirring. Let swell 1 hour. Extemporaneously add Phase D in the previous phase under stirring. Neutralize with Phase E. Put under stirring. Then add Phase F. Allow mixing at least one hour under stirring and then add Phase G. Mix well.

Examples of additional ingredients that can be added to the serum type formula in one of the phases or extemporaneously according to their hydrophobic or hydrophilic physical property at a certain % depending on their concentration and the desired effect:

LUMISHERE™: active ingredient marketed by SEDERMA (WO04/024695). It is the combination of diacétyl-boldine (DAB) encapsulated in polymethylmethacrylate microcapsules and titanium dioxide modified with manganese (TiO₂Mn). The TiO₂Mn gives the skin a unifying, mattifying and luminous effect and DAB provides a physiological Phase lightening effect. 4% of this ingredient may for example be added to the Phase F of the formulation.

REVIDRAT™: active marketed by SEDERMA that in particular improves the cohesion of the epidermis and its hydration. 2% of this ingredient may for example be added to Phase C of the formulation.

EVERMAT™: active marketed by SEDERMA (WO2007/029187), which decreases the secretion of sebum and thus participates in the treatment of oily skin. 4% of this ingredient may for example be added to Phase F of the formulation.

HALOXYL™: active marketed by SEDERMA (WO2005/102266), which improves the eye contour by reducing dark circles. 3% of this ingredient may for example be added to Phase F of the formulation.

Example 6: Lotion Form

| Ingredients | INCI names | % by weight |
|---|---|---|
| Phase A | | |
| H₂O | Water | Qsp100 |
| Phase B | | |
| Butylene Glycol | Butylene Glycol | 5.00 |
| Phenoxyethanol | Phenoxyethanol | 0.20 |
| Phase C | | |
| Crillet 1 | Polysorbate 20 | 2.00 |
| Crodamol STS | PPG-3 Benzyl Ether Myristate | 0.10 |
| Phase D | | |
| Potassium sorbate | Potassium Sorbate | 0.10 |
| Phase E | | |
| Active ingredient comprising the extract of *Globularia cordifolia* | | 2.00 |
| Phase F | | |
| Fragrance | Fragrance | 0.10 |

Procedure:

Weigh Phase A. Weigh Phase B and mix. Add Phase B into Phase A under stirring for 30 minutes. Weigh Phase C, mix until obtaining a homogenized mixture. Add Phase C into phase A+B while stirring. Add Phase D in the previous Phase. Add Phase E still under stirring; homogenise well. Weigh Phase F, mix and add to the previous Phase, mix thoroughly.

Examples of additional ingredients that can be added to the lotion type formula in one of the phases or extemporaneously according to their hydrophobic or hydrophilic physical property at a certain % depending on their concentration and the desired effect:

EYELISS™: an active sold by SEDERMA (WO2003/068141), which helps prevent and fight against the appearance of bags under the eyes. 3% of this ingredient may for example be added to Phase E of the formula.

Ac-Net™: an active sold by SEDERMA (WO2003/02828692) offering a complete treatment of oily and acne-prone skins 3% of this ingredient may for example be added to Phase E of the formula.

EVERMAT™: mentioned above. 4% of this ingredient can be for example added to Phase E of the formula.

HYDRERGY™: active marketed by SEDERMA (WO2003/02828692 long-term moisturizer and stimulates the ATP synthesis. 3% of this ingredient may for example be added to Phase E of the formula.

E) In Vivo Studies

The tests were achieved with the cream of above example 1.

Principle

The efficacy study of the cosmetic cream containing the *Globularia* extract according to the invention was performed on a panel of 20 volunteers with dull skin to assess the improvement in facial complexion; on another panel of 22 volunteers with reactive skin to demonstrate an improvement in this effect and on a panel of 14 volunteers with visible signs of ageing (wrinkles, spots, etc.) to assess the amounts of SOD and carbonylated proteins present. Several complementary methods were combined during this study:

Analysis of clarity and redness of the complexion on standardised photographs.

Analysis of skin transparency by the Transluderm™.

Analysis of skin shine and matting by the Goniolux™.

Evaluation of reduced over-reactivity of the skin with the Neurometer®.

Evaluation of the amounts of SOD and carbonylated proteins on adhesive tape strips taken from the cheek.

Protocol

Specific Inclusion Criteria for the Different Studies

Women with a dull, tired and uneven complexion were included in the complexion study. 39% of these women were smokers, a factor which is very often associated with a dull complexion.

In the skin reactivity studies, the volunteers were selected on the basis of a positive response to the stinging test and from a questionnaire revealing a sufficient sensitivity score. The volunteers were required to follow a 15-day washout period (using the placebo).

In the ageing signs study, the 14 volunteers were selected if they were over 45 years old and had multiple signs of ageing: lines, blemishes or redness. As in the previous study, a washout period was required.

For the 3 tests, no hormonal changes were allowed during the 3 months before the tests and during the tests themselves (no change in contraceptive, hormone replacement or curative therapy).

Subjects had to use only the cosmetic products provided during the study.

Types of Study and Duration

The studies were conducted single blind using non-invasive measurements on:

- 20 volunteers with dull skin (mean age 34 years old [range 20 to 48 years old]) who were randomized to apply the cream containing the *Globularia cordifolia* extract to half of their face and the placebo cream to the other half of their face.
- 22 volunteers with reactive skin (mean age 44 years old [range 25 to 64 years old]) who were randomized to apply the cream containing the *Globularia cordifolia* extract to one forearm and the placebo to the controlateral arm. The creams for this panel were slightly richer (2% glycerine added) because of the subjects' reactive skin.
- 14 volunteers with physical signs of ageing (average age 57.5 years old [range 47 to 71 years old]) were randomized to apply the cream containing the *Globularia cordifolia* extract to one cheek and the placebo cream to the controlateral cheek.

The cream containing the *Globularia cordifolia* extract or the placebo was applied by massaging into the skin twice daily for 2 months.

The study is summarized in the diagram below.

| T0 | T 1 month | T 2 months |
|---|---|---|
| Complexion measurements | | Complexion measurements |
| Neurometer® mesurements | Neurometer® measurements | |
| SOD | | SOD |
| Carbonylated proteins | | Carbonylated proteins |

Statistical tests were performed using the Student t test or with a non-parametric Wilcoxon test where necessary. In both situations, the tests were single-tailed and on paired measurements.

1.1 Study of Facial Complexion

Analysis of Clarity and Redness from Standardised Photographs

A photography system, the HeadScan (Cosm'O Laboratory) was used to take identical photographs on the two occasions. The system uses a high definition digital camera equipped with flashes and filters to obtain cross-polarized light taking a shine-free image.

For each half of the face, 5 areas were automatically extracted with the FrameScan software to calculate the Clarity (L*) and Redness (a*) indices.

The results are given in the Tables 18 and 19 below.

TABLE 18

Change in clarity of facial complexion after application for 2 months of the cream comprising the extract of *Globularia cordifolia*; (N = 20)

| | Improvement in clarity of complexion L* | |
|---|---|---|
| | T0 | T 2 months |
| PLACEBO cream | 29.86 ± 2.46 | 27.36 ± 2.17 |
| % Change (significance) | −8.4%; (p < 0.01) | |
| *Globularia cordifolia* cream | 29.88 ± 3.79 | 30.12 ± 3.39 |
| % Change (significance) | 0.8% (dns) | |
| Difference (*Globularia cordifolia* extract cream − Placebo) in variation vs. T0. | 9.2% | |
| Significance vs. placebo | p < 0.01 | |

*Physiological scale: the first 20 units of the scale represent a very dull surface; these are deducted.

The results show that complexion clarity, measured by the parameter L*, is deteriorated on the placebo side after 2 months, with a difference of 8.4% from T0 (p<0.01). On the side of the extract of *Globularia cordifolia* according to the invention, clarity remained stable during this period when skin parameters deteriorated. A marked improvement (+9.2% (p<0.01)) in facial clarity was seen against placebo.

TABLE 19

Change in redness of facial complexion after application of the cream comprising the extract of *Globularia cordifolia* for 2 months; (N = 20)

| | Improvement in Redness + a* | |
|---|---|---|
| | T0 | T 2 months |
| PLACEBO cream | 14.42 ± 2.61 | 16.89 ± 1.95 |
| % Change (significance) | 17.1% (p < 0.01) | |
| *Globularia cordifolia* extract cream | 14.28 ± 2.32 | 14.81 ± 2.07 |
| % Change (significance) | 3.7% (dns) | |
| Delta (*Globularia cordifolia* extract cream − Placebo cream) in variation vs. T0. | −13.4% | |
| Significance vs. placebo | p < 0.01 | |

In parallel, redness complexion of these volunteers increases on the placebo side during the test by +17.1%; (p<0.01). This may have been due to the different weather conditions between the two measurement times. Application of the *Globularia cordifolia* extract cream however limited this increasing trend in redness. The difference between the two sides was in favor of the side treated with the *Globularia cordifolia* extract cream: −13.4%; (p<0.01)

From the results obtained for these two parameters, fewer imperfections and redness with a more even and radiant complexion for the face can be deducted.

reflected can be broken down into specular (mirror effect) reflected light and diffuse reflected light (halo effect). The skin appears more youthful and more beautiful when the light returned is soft with less shine and more matting (halo). Results are given below in Table 21.

TABLE 21

Change in the specular light and diffuse light parameters after applying the *Globularia cordifolia* extract cream; (N = 20)

|  | Specular light (arbitrary unit) | | Diffuse light (arbitrary unit) | |
| --- | --- | --- | --- | --- |
|  | T0 | T 2 months | T0 | T 2 months |
| PLACEBO cream | 780.7 ± 8.2 | 750.2 ± 27.2 | 7.37 ± 0.06 | 8.22 ± 0.51 |
| % Change (Significance) | −3.9% (dns) | | +11.5% (dns) | |
| *Globularia cordifolia* extract cream | 777.0 ± 8.2 | 706.0 ± 28.4 | 7.39 ± 0.06 | 8.71 ± 0.51 |
| % Change (significance) | −9.1% (p < 0.02) | | +17.9% (p < 0.01) | |
| Delta (*Globularia cordifolia* extract cream − Placebo cream) in variation vs. T0. | +5.2% | | +6.4% | |
| Significance vs. placebo | p = 0.07 | | Trend (p < 0.15) | |

Analysis of Skin Transparency by TRANSLUDERM™

Skin transparency was assessed by an instrument developed by Orion Concept: the Transluderm™. This instrument consists of a 17 mm radius plate, the center of which contains a continuous spectrum white light diode which illuminates the skin. Sensors are arranged every 1.5 mm in all four directions, recording the amount of light given off by the skin. An image is taken using a high resolution camera and image analysis is performed with dedicated software. A "maximum propagation distance" parameter of light conducted through the skin is obtained from this. Understandably, transparent skin conducts light further.

Results are given in table 20 below.

TABLE 20

Change in skin transparency of measured skin by the Transluderm ™ after application of the *Globularia cordifolia* extract cream; (N = 20)

|  | Distance (mm) | |
| --- | --- | --- |
|  | T0 | T 2 months |
| PLACEBO cream | 18.90 ± 13 | 21.59 ± 11.4 |
| % Change (Significance) | +14.3% (dns) | |
| *Globularia cordifolia* extract cream | 19.1 ± 12.4 | 31.9 ± 31.9 |
| % Change (significance) | +67% (p < 0.03) | |
| Delta (*Globularia cordifolia* extract cream − Placebo cream) in variation vs. T0. | 52.7% | |
| Significance vs. placebo | p = 0.095 | |

The light was found to travel a far greater distance (+52.7% vs. placebo) indicating that skin transparency is greatly improved after applying the *Globularia cordifolia* extract cream. The previously observed effects are thus reinforced.

Analysis of Skin Radiance by the GONIOLUX™

The Goniolux™ (Orion Concept) was used to assess shine and matting parameters. This instrument quantifies the interaction between light projected onto the skin (incident light) and the behaviour of the light returned by the skin (reflected light). Reflected light is measured using multiple sensors in all directions in a three-dimensional space. The light Application of the *Globularia cordifolia* extract cream for 2 months produced a beneficial mattifying effect consisting of reduced shine (−9.1%; p<0.02 vs. T0), producing an improvement in results for this parameter (+5.2%; p<0.07 vs. placebo) combined with an increasing trend in the matt appearance (+17.9%; p<0.01 vs. T0).

Improvement in these 2 parameters produces a face which is smoother and softer in appearance.

1.2 Study of Skin Reactivity

In order to examine the improvement in volunteers' skin reactivity, an instrument called the Neurometer® was used, this instrument being used in medicine for early detection of hyper or hypo-reactivity.

The Neurometer® can be used to provide both a quantitative and qualitative characterization of changes in skin sensitivity.

The instrument stimulates nerve cells by delivering a small current to the skin until the volunteer detects something (the procedure is entirely painless). This corresponds to the individual current perception threshold (or CPT=Current Perception Threshold).

If a person can perceive currents at a higher intensity than other people, this indicates that they have a higher skin tolerance to stresses and a less reactive skin. Conversely, low perception currents indicate a more reactive skin.

There are several types of nerve fibers, (Aβ, Aδ and C fibers) which can be excited by different frequency currents. The 3 types of nerve fibers carry different information. Because of the experiences of volunteers in the inclusion tests, forearm type Aβ fibers as the model in this study was used. These large diameters, rapid conduction fibers, carry skin touch, pressure, vibration and distension information. They are associated with four types of mechano-receptors: Meissner's corpuscles, Ruffini's corpuscles, Merkel's disks and Pacini's corpuscles.

Measurements were performed automatically and double-blind in this study, ensuring very reliable results, which are particularly important for this type of individually dependent, subjective sensation. Results are given in below Table 22.

TABLE 22

Change in skin tolerability threshold after applying
the *Globularia cordifolia* extract cream; (N = 22)

|  | Aβ fibers (in mAmperes) | |
|---|---|---|
|  | T0 | T 1 months |
| PLACEBO cream | 81.82 ± 17.9 | 75.64 ± 17.9 |
| % Change (Significance) | −7.6% (dns) | |
| *Globularia cordifolia* extract cream | 69.45 ± 16.8 | 80.55 ± 22.9 |
| % Change (significance) | +16% ($p < 0.01$) | |
| Delta (*Globularia cordifolia* extract cream − Placebo cream) in variation vs. T0. | +23.6% | |
| Significance vs. placebo | $p < 0.01$ | |

The results show a slight and insignificant deterioration in the perception threshold on the placebo site which, as a result of this fall, makes the skin more reactive than at T0.

Conversely, on the site which was treated with the cream comprising the *Globularia cordifolia* extract, the perception threshold rose very significantly by +23.6%; ($p<0.01$) compared to placebo. This indicates a fall in skin reactivity after using the *Globularia cordifolia* cream according to the invention.

1.3 Studied SOD and Carbonylated Proteins on Adhesive Tape Strips

A test was conducted on volunteers with visible signs of ageing (N=14) to confirm the stimulation of SOD production seen in culture cells and in explants treated with the *Globularia cordifolia* extract cream.

After applications of the cream containing the *Globularia cordifolia* extract onto the cheek for 2 months, SOD activity measured from adhesive tape strips taken from the cheeks showed a marked improvement in activity of +19% on the site of the *Globularia cordifolia* extract cream compared to a fall of 13% on the controlateral placebo site. The difference of 32% is significant (p<0.01). Furthermore, the amounts of carbonylated proteins found on the stratum corneum cells removed by adhesive tape strips in the same study were also measured using the method of FUJITA et al, (2007). Carbonylated proteins were identified directly on the adhesive tape strips using an FTZ fluorescent label and measured with a fluorescence reader. Data was standardized by parallel measurement of total protein. The results are given below in Table 23.

TABLE 23

Change in amounts of carbonylated proteins after applying
the *Globularia cordifolia* extract cream; (N = 14)

|  | Carbonylated proteins/mg protein (fluorescence units) | | |
|---|---|---|---|
|  | T0 | T 2 months | % Change/T0 |
| PLACEBO cream | 158910 +/− 89197 | 184364 +/− 93933 | +16% |
| % Change (significance) | | | |
| *Globularia cordifolia* extract cream | 170510 +/− 77739 | 167937 +/− 77098 | −2% |
| % Change (significance) | | | |
| Delta (*Globularia cordifolia* extract cream − Placebo cream) in variation vs. T0. | | | 18% |
| Significance vs. placebo | | | $p < 0.01$ |

These results show that less carbonylated protein was collected onto the adhesive strips on the side which was treated with the *Globularia cordifolia* extract cream and that this difference was significant compared to the placebo site (−18% on the placebo side; (p<0.01).

Thus, after 2 months' application to skin with visible signs of ageing, the *Globularia cordifolia* extract cream is able to improve SOD activity and reduces amounts of carbonylated proteins present. Combined with the observations in the tests on dull skin, it can be conclude that the *Globularia cordifolia* extract cream has stimulated the skin's defences and restored its transparency and radiance. The improvement in cleansing capacity has helped to reduce reactiveness, making the skin less receptive to future stresses, as being immunized. The *Globularia cordifolia* extract cream therefore acts as a genuine anti-ageing vaccine.

The invention claimed is:

1. An in-vitro method for preparing a cellular extract of undifferentiated cells from a *Globularia cordifolia* plant, the method comprising:
   a. pre-culturing a callus cell line of the undifferentiated cells from the *Globularia cordifolia* plant in a medium to produce a cell biomass;
   b. culturing the cell biomass produced in step (a) in a bioreactor under conditions to provide an initial proliferation phase of proliferating the cell biomass in the medium, and an elicitation phase of eliciting cellular synthesis of secondary metabolites from the proliferated cell biomass; and
   c. recovering the cellular extract by lysing the cells in the cultured biomass,
      wherein the cellular extract comprises an enhanced content of phenylethanoid glycosides.

2. The method of claim 1, wherein the cell line is produced from leaf cells of said plant.

3. The method of claim 1, wherein said elicitation phase comprises culturing the cell biomass in medium depleted in sucrose and macronutrients.

4. The method of claim 1, wherein said recovering step (c) comprises lysing the cells of the cell biomass at acidic pH.

5. The method of claim 1, wherein the undifferentiated cells are cell line DSM 25009.

* * * * *